United States Patent [19]
Unger

[11] Patent Number: 5,997,898
[45] Date of Patent: *Dec. 7, 1999

[54] STABILIZED COMPOSITIONS OF FLUORINATED AMPHIPHILES FOR METHODS OF THERAPEUTIC DELIVERY

[75] Inventor: Evan C. Unger, Tucson, Ariz.

[73] Assignee: ImaRx Pharmaceutical Corp., Tucson, Ariz.

[*] Notice: This patent issued on a continued prosecution application filed under 37 CFR 1.53(d), and is subject to the twenty year patent term provisions of 35 U.S.C. 154(a)(2).

[21] Appl. No.: 08/465,868

[22] Filed: Jun. 6, 1995

[51] Int. Cl.$^6$ .............................. A61K 9/127; A61K 9/50; A61K 49/04

[52] U.S. Cl. ........................ 424/450; 424/9.51; 424/9.52; 424/489; 424/499; 424/502; 514/962; 514/963

[58] Field of Search .................................. 424/9.52, 9.5, 424/9.51, 9.321, 450, 489, 499, 502; 128/662.02; 600/458, 441; 514/962, 963; 935/54

[56] References Cited

U.S. PATENT DOCUMENTS

| | | | |
|---|---|---|---|
| 3,015,128 | 1/1962 | Sommerville et al. | 18/2.6 |
| 3,291,843 | 12/1966 | Fritz et al. | 260/614 |
| 3,293,114 | 12/1966 | Kenaga et al. | 162/168 |
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,557,294 | 1/1971 | Dear et al. | 424/342 |
| 3,594,326 | 7/1971 | Himmel et al. | 252/316 |
| 3,615,972 | 10/1971 | Morehouse et al. | 156/79 |
| 3,650,831 | 3/1972 | Jungermann et al. | 134/27 |
| 3,732,172 | 5/1973 | Herbig et al. | 252/316 |
| 3,873,564 | 3/1975 | Schneider et al. | 260/309.6 |
| 3,945,956 | 3/1976 | Garner | 260/2.5 B |
| 3,960,583 | 6/1976 | Netting et al. | 106/122 |
| 3,968,203 | 7/1976 | Spitzer et al. | 424/47 |
| 4,027,007 | 5/1977 | Messina | 424/46 |
| 4,089,801 | 5/1978 | Schneider | 252/316 |
| 4,108,806 | 8/1978 | Cohrs et al. | 521/54 |
| 4,138,383 | 2/1979 | Rembaum et al. | 260/29.7 H |
| 4,162,282 | 7/1979 | Fulwyler et al. | 264/9 |
| 4,179,546 | 12/1979 | Garner et al. | 521/56 |
| 4,192,859 | 3/1980 | Mackaness et al. | 424/5 |
| 4,224,179 | 9/1980 | Schneider | 252/316 |
| 4,229,360 | 10/1980 | Schneider et al. | 260/403 |
| 4,265,251 | 5/1981 | Tickner | 128/660 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,342,826 | 8/1982 | Cole | 435/7 |
| 4,344,929 | 8/1982 | Bonsen et al. | 424/15 |
| 4,420,442 | 12/1983 | Sands | 264/13 |
| 4,421,562 | 12/1983 | Sands et al. | 106/75 |
| 4,426,330 | 1/1984 | Sears | 260/403 |

(List continued on next page.)

FOREIGN PATENT DOCUMENTS

| | | |
|---|---|---|
| B-30351/89 | 3/1993 | Australia . |
| 0 052 575 | 5/1982 | European Pat. Off. . |
| 0 107 559 | 5/1984 | European Pat. Off. . |
| 0077752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357 163 A1 | 3/1990 | European Pat. Off. . |
| 0 361 894 | 4/1990 | European Pat. Off. . |
| 0 216 730 | 1/1991 | European Pat. Off. . |
| 0 467 031 A2 | 5/1991 | European Pat. Off. . |
| 441468 A2 | 8/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 0 614 656 A1 | 9/1994 | European Pat. Off. . |
| 0 727 225 A2 | 8/1996 | European Pat. Off. . |
| 2 700 952 | 8/1994 | France . |
| 25 21 003 | 8/1976 | Germany . |
| 62-286534 | 12/1987 | Japan . |
| 63-60943 | 3/1988 | Japan . |
| 1044680 | 10/1966 | United Kingdom . |
| 2193095 A | 2/1988 | United Kingdom . |
| WO 80/02365 | 11/1980 | WIPO . |
| WO 82/01642 | 5/1982 | WIPO . |

(List continued on next page.)

OTHER PUBLICATIONS

Lincoff et al., "Intravitreal Expansion of Perfluorocarbon Bubbles", *Arch. Ophthamol.*, 1980, 98, 1646.

Lincoff et al., "Intravitreal Longevity of Three Perfluorocarbon Gases", *Arch. Ophthalmol.*, 1980, 98, 1610–1611.

Lincoff et al., "The Perfluorocarbon Gases in the Treatment of Retinal Detachment", *Ophthalmology*, 1983, 90(5), 546–551.

Gardner et al., "A Survey of Intraocular Gas Use in North America", *Arch. Ophthamol.*, 1998, 106, 1188–1189.

Unger et al., "Liposomal MR Contrast Agents", *J. Liposome Research*, 1994, 4(2), 811–834.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

(List continued on next page.)

*Primary Examiner*—Jose' G. Dees
*Assistant Examiner*—Michael G. Hartley
*Attorney, Agent, or Firm*—Woodcock Washburn Kurtz MacKiewicz & Norris LLP

[57] ABSTRACT

Stabilized compositions comprising, in combination with a gas, a fluorinated amphiphilic compound. The compositions are particularly suitable for use in diagnostic applications, including ultrasound. The compositions can take the form of vesicular compositions, such as micelles and liposomes.

24 Claims, No Drawings

U.S. PATENT DOCUMENTS

| | | | |
|---|---|---|---|
| 4,427,649 | 1/1984 | Dingle et al. | 424/38 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,530,360 | 7/1985 | Duarte | 128/419 F |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon | 424/1 |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,663,161 | 5/1987 | Mannino et al. | 424/89 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,693,999 | 9/1987 | Axelsson et al. | 514/174 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,834,964 | 5/1989 | Rosen | 424/9 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,918,065 | 4/1990 | Stindl et al. | 514/179 |
| 4,919,895 | 4/1990 | Heldebrant et al. | 422/129 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,984,573 | 1/1991 | Leunbach | 128/653 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 5,000,960 | 3/1991 | Wallach | 424/450 |
| 5,004,611 | 4/1991 | Leigh | 424/450 |
| 5,008,050 | 4/1991 | Cullis et al. | 264/4.3 |
| 5,008,109 | 4/1991 | Tin | 424/422 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,107,842 | 4/1992 | Levene et al. | 128/662.02 |
| 5,114,703 | 5/1992 | Wolf et al. | 424/5 |
| 5,123,414 | 6/1992 | Unger | 128/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,348 | 3/1993 | Schweighardt et al. | 436/173 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,247,935 | 9/1993 | Cline et al. | 128/653.2 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,339,814 | 8/1994 | Lasker | 128/653.4 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,354,549 | 10/1994 | Klaveness et al. | 424/3 |
| 5,358,702 | 10/1994 | Unger | 424/9 |
| 5,362,477 | 11/1994 | Moore et al. | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |
| 5,485,839 | 1/1996 | Aida et al. | 128/653.1 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,539,814 | 7/1996 | Shoji | 379/215 |
| 5,540,909 | 7/1996 | Schutt | 424/9.52 |
| 5,542,935 | 8/1996 | Unger et al. | 604/190 |
| 5,545,396 | 8/1996 | Albert et al. | 424/93 |
| 5,547,656 | 8/1996 | Unger | 424/9.4 |
| 5,552,133 | 9/1996 | Lambert et al. | 424/9.52 |
| 5,552,155 | 9/1996 | Bailey et al. | 424/450 |
| 5,556,372 | 9/1996 | Talish et al. | 601/2 |
| 5,556,610 | 9/1996 | Yan et al. | 424/9.52 |

| | | | |
|---|---|---|---|
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,558,856 | 9/1996 | Klaveness et al. | 424/9.37 |
| 5,560,364 | 10/1996 | Porter | 128/662.02 |
| 5,562,893 | 10/1996 | Lohrmann | 424/9.52 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,448 | 10/1996 | Wong et al. | 424/9.45 |
| 5,569,449 | 10/1996 | Klaveness et al. | 424/9.51 |
| 5,571,797 | 11/1996 | Ohno et al. | 514/44 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,593,680 | 1/1997 | Bara et al. | 424/401 |
| 5,595,723 | 1/1997 | Quay | 424/9.5 |
| 5,605,673 | 2/1997 | Schutt et al. | 424/9.51 |
| 5,606,973 | 3/1997 | Lambert et al. | 128/662.02 |
| 5,612,057 | 3/1997 | Lanza et al. | 424/450 |
| 5,612,318 | 3/1997 | Weichselbaum et al. | 514/44 |
| 5,614,169 | 3/1997 | Klaveness et al. | 424/9.52 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,672,585 | 9/1997 | Pierschbacher et al. | 514/11 |
| 5,676,928 | 10/1997 | Klaveness et al. | 424/9.32 |
| 5,679,459 | 10/1997 | Riess et al. | 428/402.2 |
| 5,686,060 | 11/1997 | Schneider et al. | 424/9.52 |
| 5,686,102 | 11/1997 | Gross et al. | 424/450 |
| 5,707,606 | 1/1998 | Quay | 424/9.52 |
| 5,707,607 | 1/1998 | Quay | 424/9.52 |
| 5,711,933 | 1/1998 | Bichon et al. | 424/9.52 |
| 5,716,597 | 2/1998 | Lohrmann et al. | 424/9.5 |
| 5,732,707 | 3/1998 | Widder et al. | 128/661.08 |
| 5,733,527 | 3/1998 | Schutt | 424/9.52 |
| 5,740,807 | 4/1998 | Porter | 128/662.02 |
| 5,804,162 | 9/1998 | Kabalnov et al. | 424/9.51 |
| 5,840,023 | 11/1998 | Oraevsky et al. | 600/407 |
| 5,855,865 | 1/1999 | Lambert et al. | 424/9.52 |
| 5,858,399 | 1/1999 | Lanza et al. | 424/450 |
| B1 4,229,360 | 11/1991 | Schneider et al. | 260/403 |

FOREIGN PATENT DOCUMENTS

| | | |
|---|---|---|
| WO 84/02909 | 8/1984 | WIPO . |
| US85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/15284 | 9/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/17514 | 10/1992 | WIPO . |
| WO 92/21382 | 12/1992 | WIPO . |
| WO 92/22249 | 12/1992 | WIPO . |
| WO 92/22298 | 12/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/00110 | 1/1994 | WIPO . |
| WO 94/06477 | 3/1994 | WIPO . |
| WO 94/07539 | 4/1994 | WIPO . |
| WO 94/09829 | 5/1994 | WIPO . |
| WO 94/16739 | 8/1994 | WIPO . |
| WO 94/21302 | 9/1994 | WIPO . |
| WO 94/28780 | 12/1994 | WIPO . |
| WO 94/28873 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 95/24184 | 9/1995 | WIPO . |
| WO 96/04018 | 2/1996 | WIPO . |
| WO 96/09793 | 4/1996 | WIPO . |
| WO 96/36286 | 11/1996 | WIPO . |
| WO 96/40281 | 12/1996 | WIPO . |
| WO 98/00172 | 1/1998 | WIPO . |

OTHER PUBLICATIONS

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. 575–578 (1986).

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1992, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob Biotech.*, 22(4), pp. 1403–1408 (1994).

Chang et al., "Semipermeable Aqueous Microcapsules", *Canadian J. of Phys. and Pharm.*, 1966, 44, 115–128.

Chang, "Semipermeable Microcapsules", *Science*, 1964, 146, 524–525.

Deasy, *Microencapsulation and Related Drug Processes*, 1983, vol. 20, Chs. 9 and 10, 195–240 (Marcel Dekker, Inc., NY).

Yeung et al., "Preparation of Microencapulated Liposomes", *J. Microencapsulation*, 1988, 5, 331–337.

Mattrey et al., *Gas Emulsions and Ultrasound Contrast Agents; Prelimiary Results in Rabbits and Dogs, Investigatvie Radiology*, vol. 29, Jun. Supp. 2, pp. S139–S141, 1994.

Feinstein, Steven B., "Myocardial Perfusion Imaging: Contrast Echocardiography Today and Tomorrow," *Journal of the American College of Cardiology*, 8(1):251–253 (1986).

Keller et al., "The Behavior of Sonicated Albumin Microbubbles Within the Microcirulation: A Basis for Their Use During Myocardial Contrast Echocardiography", *Circulation Res.*, 65(2):458–465 (1989).

Lincoff et al., "Perfluoro–n–butane: A Gas for Maximum Duration Retinal Tamponade," *Arch. Ophthalmology*, 101:460–462 (1983).

*Remington's Pharmaceutical Sciences*, John Hoover, managing ed., Mack Publishing Company, Easton, PA, pp. 295–298; 736; 1242–1244.

*Handbook of Pharmaceutical Excipients*, American Pharmaceutical Association, Washington, D.C. and The Pharmaceutical Society of Great Britian, London, England, pp. 181–183 (1986).

Miller et al., "Physiochemical Approaches to the Mode of Action of General Anesthetics," *J. Amer. Soc. Anesthesiologists*, 36(4): 339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Bio–chemistry*, vol. 9, No. 3, pp. 525–532 (1970).

Stelmashok et al., *Koordinatsionnay Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hop et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochmica et Biophysica Acta*, vol. 858, pp. 161–168 (1886).

Cheng et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Anti–biotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocar–diography, I: In Vitro Development and Quantitative Analysis of Echo Contrast Agents", *JACC*, vol. 3, No. 1, pp. 14–20 (1984).

Ten Cate et al., "Two–Dimensional Contrast Echocar–diography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No.2, pp. 326–335 (1988).

Anderson et al., "Manganese (III) Complexes in Oxidative Decarboxylation of Acids", *J. Am. Chem. Soc.*, vol. 92, No.8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience Sonicator™*, Heat Systems–Ultrasonics, Inc. (1987).
M. Ostro, "Liposomes", Marcel Dekker, New York, pp. 102–103 (1983).
Fukuda et al., "Polymer–Encased Vesicles Derived from Diotadecyldimethylammonium Methacrylate", *J. Am. Chem. Soc.*, vol. 108, pp. 2321–2327 (1986).
Regen, "Polymerized Vesicles", *J. Am. Chem. Soc.*, vol. 102, pp. 6638–6640 (1989).
Rose, A. and Rose, E., "The Condensed Chemical Dictionary", Reinhold Publishing, New York, pp. 728 and 743 (1966).
A.G. Belykh, *Farmakol Toksikol. (MOSC)*, vol. 44(3), pp. 322–326 (1981) (abstract).
J. Vion–Dury et al., *J. Pharmacol. Exper. Ther.*, vol. 250(3), pp. 1113–1118 (1989) (abstract).
M.R. Zalutsky et all., *Invest. Radiol.*, vol. 22(2), pp. 141–147 (1987) (abstract).
Crowe et al., *Archives of Biochemistry and Biophysics*, vol. 242, pp. 240–247 (1985).
Crowe et al., *Archives of Biochemistry and Biophysics*, vol. 220, pp. 477–484 (1983).
Dorland's Illustrated Medical Dictionary, p. 946, 27th ed. (W.B. Saunders Company, Philadelphia 1988).
*Liposome Technology*, Gregoriadis, G., ed., vol. I, pp. 1–18, 29–35, 51–65 and 79–107 (CRC Press Inc., Boca Raton, FL, (1984).
Madden et al., *Chemistry and Physics of Lipids*, vol. 53, pp. 37–46 (1990).
Sinkula et al., *J. Pharm. Sci.*, vol. 64, pp. 181–210 (1975).
Chapman et al., "Biomembrane Phase Transitions", *J. Biol. Chem.*, 1974, 249:2512–2521.
Hug et al., "Liposomes for the Transformation of Eukaryotic Cells", *Biochimica et Biophysica Acta*, 1991, 1097:1–17.
Marsh, *CRC Handbook of Lipid Bilayers* (CRC Press, Boca Raton, FL 1990) pp. 139–141.
Szoka et al., "Procedure for Preparation of Liposomes With Large Internal Aqueous Space . . . ", *Proc. Natl. Acad. Sci.* 1978, 75:4194–4198.
Acoustic Imaging; AI5200; Convex Curved Linear Array Ultrasound Transducers Operator's Manual, Nov. 20, 1989, 4700–0003–1C, p. 4.
Bangham et al., "Diffusion of Univalent Ions across the Lamellae of Swollen Phospholipids", *J. Mol. Biol.*, 1965, 13:238–252.
Carson et al., "Ultrasonic Power and Intensities Produced by Diagnostic Ultrasound Equipment", *Ultrasound in Med. & Biol.* 3, 1978, 341–350.
deGier et al., "Relations Between Liposomes and Biomembranes", *Annals of The New York Academy of Sciences*, 1978, 308:85–99.
Felgner et al., "Lipofection: A highly efficient, lipid–mediated DNA–transfection procedure", *Proc. Natl. Acad. Sci.*, 1987, 84:7413–7417.
Gabizon et al., "Liposome formulations with prolonged circulation time in blood and enhanced uptake by tumors", *Proc. Natl. Acad. Sci.*, 1988, 85:6949–6953.
Garelli, et al., *Biochimica et Biophysica Acta*, vol. 1127:41–48 (1992).
Kawai et al., "New Procedure for DNA Transfection with Polycation and Dimethyl Sulfoxide", *Molecular and Cellular Biology*, 1984, 4:1172–1174.
Kuo et al., "Metallocene Antitumor Agents. Solution and Solid–State Molybdenocene Coordination . . . ", *J. Am. Chem. Soc.*, 1991, 113:9027–9045.

*Mammalian Cell Biotechnology: A Practical Approach*, M. Butler, 1991 (Oxford University Press, New York), pp. 57–70.
Mathiowitz et al., "Photochemical Rupture of Microcapsules: A Model System", *Journal of Applied Polymer Science*, 1981, 26:809–822.
May et al., "Cationic Liposomes Enable Bovine Herpesvirus Type 2 DNA to Infect Cells", *Acta virol.*, 1991, 35:107.
Poznansky et al., "Biologica Approaches to the Controlled Delivery of Drugs: A Critical Review", *Pharmacol, Rev.*, 1984, 36:277–336.
Sato et al., "Recent Aspects in the Use of Liposomes in Biotechnology and Medicine", *Prog. Lipid Res.* 1992, 4:345–372.
Simons et al., "Antisense c–myb oligonucleotides inhibit intimal arterial smooth muscle cell accumulation in vivo", *Nature*, 1992, 359:67–70.
Thompson, Larry, "At Age 2, Gene Therapy Enters a Growth Phase", *Science* 1992, 258:744–746.
Trubetskoy et al. "Cationic liposomes enhance targeted delivery and expression of exogenous DNA . . . ", Biochimica et Biophysica Acta 1992, 131:311–313.
Umemura et al., "Studies on Sonodynamic Cancer Therapy", *IEEE*, 1992, O–7803–0785, pp. 354–355.
Williams, "Human Gene Therapy: Searching for Better Vectors", *ASM News* [American Society for Microbiology] 1992, 58:67–69.
Woodle et al., "Versatility in lipid compositions showing prolonged circulation . . . ", *Biochimica et Biophysica Acta* 1992, 1105:193–200.
Zhou et al., "Targeted delivery of DNA by liposomes and polymers", *J. of Controlled Release* 1992, 19:269–274.
Mathiowitz et al., "Polyanhydride Microspheres as Drug Carriers", *Journal of Applied Polymer Science*, vol. 35, pp. 755–774 (1988).
Sankaram et al., "Cholesterol–Induced Fluid–Phase Immiscibility in Membranes", *Proc. Natl. Acad. Sci.*, vol. 88, pp. 8686–8690 (1991).
*Scientific Apparatus Catalog* 92/93 (VWR Scientific, 1991), "Syringes", pp. 1511–1513; Filtration, Syringe Filters, pp. 766–768; Filtration, Membranes, pp. 750–753; Filtration, Filter Holders, p. 744.
Gramiak et al., *Radiology*, "Detection of Intracardiac Blood Flow by Pulsed Echo–Ranging", pp. 415–418 (1971).
Feigenbaum et al., *Circulation*, "Identification of Ultrasound Echoes from the Left Ventricle by Use of Intracardiac Injections of Indocyanine Green", vol. XL1, pp. 615–621 (1970).
Santaella, et al., *FEBS 13463*, "Extended In Vivo Blood Circulation Time of Fluorinated Liposomes", vol. 336, No. 3, pp. 481–484 (1993).
Brown and Langer, *Annual Review Medicine*, 1988, 39:221 29, Annual Review, Inc., "Transdermal Delivery of Drugs", pp. 221–229.
Moseley, et al., *Microbubbles: A Novel MR Susceptibility Contrast Agent*, abstract, 1991 Napa, California Meeting of the Society for Magnetic Resonance in Medicine.
Santella, C., "New Perfluoroalkylated Phospholipids as Injectable Surfactants: Synthesis, Preliminary Physiochemical and Biocompatibility Data", *New Journal of Chemistry*, 15, 685–692 (1991).
Hirt, et al., "Zur Synthese der Phosphatide Eine neue Synthese der Lecithine", *Pharm. Acata. Helv.*, 33, 349–356 (1958).

Hansen, et al., "An Improved Procedure for the Synthesis of Choline Phospholipids via 2–Bromoethyl Dichlorophosphate[1]", *Lipids,* 17, 453–459 (1982).

Eibl, "Phospholipid synthesis: Oxazaphospholanes and dioxaphospholanes as intermediates", *Proc. Natl. Acad. Sci. USA,* 75, 4074–4077 (1978).

Fleischer, *Methods Enzymology,* vol. 98, *Biomembranes,* pp. 260–266 (1983).

Miller, *Ultrasonics* (Sep. 1981), "Ultrasonic detection of resonant cavitation bubbles in a flow tube by their second–harmonic emissions," pp. 217–224.

Barnhart et al., "Characteristics of Albunex™: Air–Filled Microspheres for Echocardiography Contrast Enhancement," *Invest. Radiol.,* 1990, 25, S162–164.

Levene et al., "Characterization of Albunex™," *J. Acoust. Soc. Am.,* 1990, 87(Suppl. 1), 569–570.

Villanueva et al., "Characterization of Spatial Patters of Flow Within the Reperfused Myocardium by Myocardial Contrast Echocardiography", *Circulation,* 1993, 88(6), 2596–2606.

Sekins et al., "Lung Cancer Hyperthermia via Ultrasound and PFC Liquids", *Published in Proceedings of 5th International Symposium on Hyperthermia Oncology, Kyoto, Japan,* Aug. 29–Sep. 3, 1998, 3 pages.

Pietersen, "A New Warning System for Fires of Electrical Origin", *CERN European Organization for Nuclear Research, Health and Safety Division,* Mar. 1977, 1–5.

Nomura et al., "US Contrast Enhancement of Hepatic Tumor with Helium Gas Microbubbles: A Preliminary Report", *Jpn. J. Med. Ultrasonics,* 1991, 18(5), 28–35 (Japanese with English language abstract).

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography,* 1998, 11(1), 36–46.

Regen et al., "Polymerized Phosphatidylcholine Vesicles Synthesis and Characterization", *J. Am. Chem. Soc.,* 1982, 104(3), 191–195.

Wei et al., "Quantification of Myocardial Blood Flow with Ultrasound–Induced Destruction of Microbubbles Administered as a Constant Venous Infusion", *Circulation,* 1998, 97, 473–483.

Hynynen et al., "The Usefulness of a Contrast Agent and Gradient Recalled Acquisition in a Steady–State Imaging Sequence for Magnetic Resonance Imaging–Guided Noninvasive Ultrasound Surgery", *Investigative Radiology,* 1994, 29(10), 897–903.

Lejbkowicz et al., "The response of normal and malignant cells to ultrasound in vitro", Database *BIOSIS,* No. 1993:95122245 (abstract only).

Jackson et al., "Effect of ultrasound therapy on the repair of Achilles tendon injuries in rats", *Med. Sci. Sports Exercise,* 1991, 23(2), 171–176.

Maxweel, "Therapeutic Ultrasound: Its Effects on the Cellular and Molecular Mechanisms of Inflammation and Repair", *Physiotherapy,* 1992, 78(6), 421–426.

Tuncay et al., "Expression of Genes Associated with Tissue Remodeling Upon Ultrasound Perturbation in the Gingival Fibroblast", *J. Dental Res.,* 1996, 75, 143, (abstract only).

Wang et al., "Low Intensity Ultrasound Treatment Increases Strength in a Rat Femoral Fracture Model", *J. Orthopaedic Res.,* 1994, 12(1), 40–47.

Yang et al., "Exposure to Low–Intensity Ultrasound Increases Aggrecan Gene Expression in a Rat Femur Fracture Model", *J. Orthopaedic Res.,* 1996, 14(5), 802–809.

Young et al., "Effect of therapeutic ultrasound on the healing of full–thickness excised skin lesions", *Ultrasonics,* 1990, 28(3), 175–180.

Young et al., "The Effect of Therapeutic Ultrasound on Angiogenesis", *Ultrasound Med. Biol.,* 1990, 16(3), 261–269.

STABILIZED COMPOSITIONS OF FLUORINATED AMPHIPHILES FOR METHODS OF THERAPEUTIC DELIVERY

FIELD OF THE INVENTION

The present invention relates to novel compositions for ultrasound. More particularly, the present invention relates to novel compositions of fluorinated amphiphilic compounds for use as contrast agents for ultrasound.

BACKGROUND OF THE INVENTION

Ultrasound is a valuable diagnostic imaging technique for studying various areas of the body including, for example, the vasculature, such as tissue microvasculature. Ultrasound provides certain advantages relative to other diagnostic techniques. For example, diagnostic techniques involving nuclear medicine and X-rays generally results in exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive as compared, for example, to computed tomography (CT) and magnetic resonance imaging (MRI), which require elaborate and expensive equipment.

Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including, for example, the constituents and the density of the particular tissue being observed. The differentially reflected waves are detected, typically with a transducer that can detect sound waves having a frequency of one megahertz (MHz) to ten MHz. The detected waves can be integrated, quantitated and converted into an image of the tissue being studied.

Ultrasound imaging techniques typically involve the use of contrast agents. Contrast agents are used to improve the quality and usefulness of images which are obtained via ultrasound. Exemplary contrast agents include, for example, suspensions of solid particles, emulsified liquid droplets, and gas-filled bubbles. See, e.g., Hilmann et al., U.S. Pat. No. 4,466,442, and published International Patent Applications WO 92/17212 and WO 92/21382.

The quality of images produced from ultrasound has improved significantly. Nevertheless, further improvement is needed, particularly with respect to images involving vasculature in tissues that are perfused with a vascular blood supply. Accordingly, there is a need for improved ultrasound techniques, including improved contrast agents, which are capable of providing medically useful images of the vasculature and vascular-related organs.

The reflection of sound from a liquid-gas interface is extremely efficient. Accordingly, bubbles, including gas-filled bubbles, are useful as contrast agents. The term "bubbles", as used herein, refers to vesicles which are generally characterized by the presence of one or more membranes or walls surrounding an internal void that is filled with a gas or a precursor thereto. Exemplary bubbles include, for example, liposomes, micelles and the like. As discussed more fully hereinafter, the effectiveness of bubbles as contrast agents depends upon various factors, including, for example, the size, elasticity and/or stability of the bubble.

With respect to the effect of bubble size, the signal that is reflected off of a bubble is a function of the radius ($r^6$) of the bubble (Rayleigh Scatterer). Thus, a bubble having a diameter of 4 micrometer ($\mu$m) possesses about 64 times the scattering ability of a bubble having a diameter of 2 $\mu$m. Thus, generally speaking, the larger the bubble, the greater the reflected signal.

However, bubble size is limited by the diameter of capillaries through which the bubbles must pass. Contrast agents which comprise bubbles having a diameter of greater than 10 $\mu$m are generally dangerous since microvessels may be occluded. Accordingly, it is desired that greater than about 99% of the bubbles in a contrast agent have a diameter of less than 10 $\mu$m. Mean bubble diameter is important also, and should be greater than 1 $\mu$m, with greater than 2 $\mu$m being preferred. The volume weighted mean diameter of the bubbles should be about 7 to 10 $\mu$m.

Bubble elasticity is also important because highly elastic bubbles can deform, as necessary, to "squeeze" through capillaries. This decreases the likelihood of occlusion. In addition, resonance is more easily induced in bubbles having enhanced elasticity. This can be advantageous in that resonating bubbles typically generate sound emissions at frequencies in the subharmonic regime (based on multiples of 0.5) or in the supra- or ultraharmonic regime (based on multiples of 2). The supraharmonic regime, including second harmonic imaging, is desirable in ultrasound since background noise is substantially eliminated. Elastic bubbles can therefore be used to produce desirable second harmonic images.

The effectiveness of a contrast agent involving bubbles is also dependent on the bubble concentration. Generally, the higher the bubble concentration, the greater the reflectivity of the contrast agent.

Another important characteristic which is related to the effectiveness of bubbles as contrast agents is bubble stability. As used herein, particularly with reference to gas-filled bubbles, "bubble stability" refers to the ability of bubbles to retain gas entrapped therein after exposure to a pressure greater than atmospheric pressure. To be effective as contrast agents, bubbles generally need to retain an amount of the entrapped gas in vivo. It is also highly desirable that, after release of the pressure, the bubbles return to their original size. This is referred to generally as "bubble resilience."

Bubbles which lack desirable stability provide poor contrast agents. If, for example, bubbles release the gas entrapped therein in vivo, reflectivity is diminished. Similarly, the size of bubbles which possess poor resilience will be decreased in vivo, also resulting in diminished reflectivity.

The stability of bubbles disclosed in the prior art is generally inadequate for use as contrast agents. For example, the prior art discloses bubbles, including gas-filled liposomes, which comprise lipoidal walls or membranes. See, e.g., Ryan et al., U.S. Pat. Nos. 4,900,540 and 4,544,545; Tickner et al., U.S. Pat. No. 4,276,885; Klaveness et al., WO 93/13809 and Schneider et al., EPO 0 554 213 and WO 91/15244. The stability of the bubbles disclosed in these references is poor in that as the solutions in which the bubbles are suspended become diluted, for example, in vivo, the walls or membranes of the bubbles are thinned. This results in a greater likelihood of rupture of the bubbles.

Various attempts have been made to improve bubble stability. Such attempts have included, for example, the preparation of bubbles in which the membranes or walls thereof are apparently strengthened via crosslinking. See, e.g., Giddey et al., U.S. Pat. No. 5,310,540 and Klaveness et al., WO 92/17212, in which there are disclosed bubbles which comprise proteins crosslinked with crosslinking agents.

Prior art techniques for stabilizing bubbles, including the use of crosslinked materials, suffer from various drawbacks. For example, the crosslinked materials described, for example, in Giddey et al., U.S. Pat. No. 5,310,540 and Klaveness et al., WO 92/17212, lack biocompatibility or possess unknown metabolic fates. Added costs are also incurred with the use of additional materials and process steps necessary for crosslinking. In addition, crosslinking can impart rigidity to the membranes or walls of the bubbles. This results in bubbles having reduced elasticity and, therefore, a decreased ability to deform and pass through capillaries. Thus, there is a greater likelihood of occlusion of vessels with prior art contrast agents that are stabilized via crosslinking.

Accordingly, new and/or better stabilized contrast agents and methods for providing same are needed. The present invention is directed to this, as well as other, important ends.

SUMMARY OF THE INVENTION

The present invention is directed, in part, to stabilized compositions of a gas and a sulfonated or phosphorylated fluorinated amphiphilic compound. Specifically, in one aspect, the present invention relates to a stabilized composition comprising, in combination with a gas, a compound of the formula

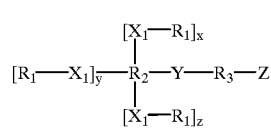

(I)

wherein:

each of x, y and z is independently 0 or 1;

each $X_1$ is independently —O—, —S—, —SO—, —SO$_2$—, —NR$_4$—, —C(=X$_2$)—, —C(=X$_2$)—O—, —O—C(=X$_2$)—, —C(=X$_2$)—NR$_4$— or —NR$_4$—C(=X$_2$)—;

$X_2$ is O or S;

Y is a direct bond or —X$_3$—M(=O)(OR$_5$)$_q$—O—, where q is 1 or 2;

$X_3$ is a direct bond or —O—;

M is P or S;

Z is hydrogen, the residue of a hydrophilic polymer, a saccharide residue or —N(R$_6$)$_r$, where r is 2 or 3;

each $R_1$ is independently alkyl of 1 to about 30 carbons or fluorinated alkyl of 1 to about 30 carbons;

$R_2$ is a direct bond or an alkylene linking group of 1 to about 10 carbons;

$R_3$ is a direct bond or an alkylene diradical of 1 to about 10 carbons;

each of $R_4$ and $R_5$ is independently hydrogen or alkyl of 1 to about 8 carbons; and each $R_6$ is independently hydrogen, alkyl of 1 to about 8 carbons or a residue of a hydrophilic polymer; provided that at least one of x, y and z is 1, at least one of $R_1$ is fluorinated alkyl of 1 to about 30 carbons and when $R_2$ is a direct bond, at least two of x, y and z are 0. In certain embodiments, the composition may further comprise, as desired, a gaseous precursor. Also, if desired, the composition may further comprise a bioactive agent.

Another aspect of the invention relates to compositions comprising, in combination with a gas, a compound of the formula

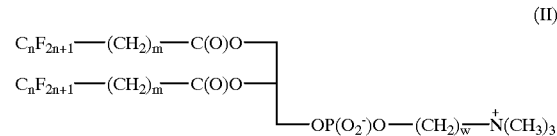

(II)

wherein:

m is 0 to about 18;

n is 1 to about 12; and w is 1 to about 8.

Yet another aspect of the invention relates to a method for the reparation of a stabilized composition of a fluorinated amphiphilic compound and a gas. The method comprises agitating an aqueous mixture of a fluorinated amphiphilic compound in the presence of a gas.

Still another aspect of the invention relates to a method of providing an image of an internal region of a patient. The method comprises administering to the patient a contrast medium comprising a stabilized composition comprising a gas and a fluorinated amphiphilic compound. The method further comprises scanning the patient using ultrasound to obtain visible images of the region.

Another aspect of the invention relates also to a method of providing an image of an internal region of a patient. This method comprises administering to the patient a vesicular composition comprising, in an aqueous carrier, vesicles comprising a fluorinated amphiphilic compound and a gas or gaseous precursor. The method also involves scanning the patient using ultrasound to obtain a visible image of any diseased tissue in the patient.

Yet another aspect of the invention relates to a method for diagnosing the presence of diseased tissue in a patient. The method involves administering to the patient a contrast medium comprising a stabilized composition comprising a gas and a fluorinated amphiphilic compound. The method further involves scanning the patient using ultrasound to obtain visible images of any diseased tissue in the patient.

Still another aspect of the invention relates to a method for the therapeutic delivery in vivo of a bioactive agent. The method comprises administering to a patient a therapeutically effective amount of a formulation which comprises, in combination with a bioactive agent, a stabilized composition of a fluorinated amphiphilic compound and a gas.

These and other aspects of the invention will become more apparent from the present specification and claims.

DETAILED DESCRIPTION OF THE INVENTION

As employed above and throughout the disclosure, the following terms, unless otherwise indicated, shall be understood to have the following meanings.

"Amphiphile" or "amphiphilic compound" refers to a synthetic or naturally-occurring compound having a water-soluble, hydrophilic portion and a water-insoluble, hydrophobic portion. Preferred amphiphilic compounds are characterized by a polar head group, for example, a phosphatidylcholine group, and one or more nonpolar, aliphatic chains, for example, palmitoyl groups. "Fluorinated amphiphile" refers to an amphiphilic compound in which at least one hydrogen atom of the amphiphilic compound is replaced with a fluorine atom. In preferred form, the fluorinated amphiphilic compounds are polyfluorinated. "Polyfluorinated", as used herein, refers to amphiphilic compounds which contain two or more fluorine atoms. In certain preferred embodiments of the present invention, the amphiphilic compounds comprise a lipid. "Lipid", as used herein, refers to materials, including fats and fat-derived materials, which are relatively insoluble in water but relatively soluble in organic solvents, such as benzene, chloroform, acetone and ether. Lipids include, for example, fatty acids, fatty acid esters, neutral fats, phosphatides (phospholipids), glycolipids, fatty alcohols, sterols, waxes, terpenes and steroids. As discussed in detail below, certain preferred lipid compounds are phosphorylated and contain phosphate groups, for example, $PO_4$ groups, and certain other preferred lipid compounds are sulfated and contain sulfate groups, for example, $SO_4$ groups.

"Amphipathy" refers to the simultaneous attraction and repulsion in a single molecule or ion containing one or more groups having an affinity for the phase or medium in which they are dissolved, emulsified and/or suspended, together with one or more groups that tend to be expelled from the involved phase or medium.

"Stabilized" refers to compositions which have been formulated as a mixture of finely divided colloidal particles floating in a liquid with minimal aggregation. As discussed in detail below, certain preferred embodiments of the present invention involve compositions of stabilized vesicles. In this context, the term "stabilized" refers to vesicles which are substantially resistant to degradation that is caused, for example, by the loss of structural or compositional integrity in the walls of the vesicles and/or by the loss of any significant portion of a gas or gaseous precursor encapsulated within the vesicle.

"Amphiphilic composition" refers to a composition which comprises an amphiphilic compound. Exemplary amphiphilic compositions include suspensions, emulsions and vesicular compositions.

"Suspension" refers to a mixture, dispersion or emulsion of finely divided colloidal particles floating in a liquid. The particles may be solid, liquid or gaseous.

"Emulsion" refers to a mixture of two or more liquids and is generally in the form of a colloidal mixture.

"Vesicle" refers to a spherical entity which is characterized by the presence of an internal void. Preferred vesicles are formulated from amphiphilic compounds, including lipids. In any given vesicle, the amphiphilic compounds may be in the form of a monolayer or bilayer, and the mono- or bilayer amphiphiles may be used to form one or more mono- or bilayers. In the case of more than one mono- or bilayer, the mono- or bilayers are generally concentric. The vesicles described herein include such entities commonly referred to as liposomes, micelles, bubbles, microbubbles, microspheres and the like. Thus, the amphiphilic compounds may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

"Liposome" refers to a generally spherical cluster or aggregate of amphiphilic compounds, including lipid compounds, typically in the form of one or more concentric layers, for example, bilayers. They may also be referred to herein as vesicles or amphiphilic vesicles.

"Gas filled vesicles" refers to vesicles in which there is encapsulated a gas. "Gaseous precursor filled vesicles" refers to vesicles in which there is encapsulated a gaseous precursor. The vesicles may be minimally, partially or substantially completely filled with the gas and/or gaseous precursor. In preferred embodiments, the vesicles are substantially completely filled with the gas and/or gaseous precursor.

"Vesicular composition" refers to a composition of vesicles that is prepared from amphiphilic compounds.

"Amphiphilic formulation" refers to a composition which comprises an amphiphilic compound and a bioactive agent.

"Vesicle formulation" refers to a composition which comprises vesicles and a bioactive agent.

"Patient" refers to animals, including mammals, preferably humans.

"Biocompatible" refers to materials which are generally not injurious to biological functions and which will not result in any degree of unacceptable toxicity, including allergenic responses and disease states.

"Bioactive agent" refers to a substance which is used in connection with an application that is therapeutic or diagnostic in nature, such as in methods for diagnosing the presence or absence of a disease in a patient and/or in methods for the treatment of disease in a patient. As used herein, "bioactive agent" refers also to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids and genetic material, including nucleosides, nucleotides and polynucleotides.

"Diagnostic agent" refers to any agent which is used in connection with methods for diagnosing the presence or absence of a disease in a patient. Exemplary diagnostic agents include, for example, contrast agents for use in connection with ultrasound, magnetic resonance imaging or computed tomography of a patient.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

"Pharmaceutical" or "drug" refers to any therapeutic or prophylactic agent which is used in the treatment, including the prevention, diagnosis, alleviation, or cure, of a malady, affliction, disease or injury in a patient. Therapeutically useful peptides, polypeptides and polynucleotides are included within the meaning of the term pharmaceutical or drug.

"Polymer", as used herein, refers to molecules formed from the chemical union of two or more repeating units. Accordingly, included within the term "polymer" are, for example, dimers, trimers and oligomers.

"Aliphatic" refers to one of the major groups of organic compounds, characterized by straight- or branched-chain arrangement of the constituent carbon atoms. Aliphatic hydrocarbons comprise three subgroups: (1) paraffins, including the alkanes; (2) olefins, including the alkenes, which contain carbon-carbon double bonds; and (3) acetylenes, including the alkynes, which contain carbon-carbon triple bonds.

"Alkyl" refers to an aliphatic hydrocarbon group which may be straight or branched having 1 to about 30 carbon atoms. "Lower alkyl" refers to an alkyl group having 1 to about 8 carbon atoms. "Higher alkyl" refers to an alkyl group having about 10 to about 30 carbon atoms. The alkyl group may be optionally substituted with one or more alkyl group substituents which may be the same or different, where "alkyl group substituent" includes, for example, halo, aryl, hydroxy, alkoxy, aryloxy, alkyloxy, alkylthio, arylthio, carboxy alkoxycarbonyl, oxo and cycloalkyl. There may be optionally inserted along the alkyl group one or more oxygen, sulphur or substituted nitrogen atoms, wherein the nitrogen substituent is lower alkyl. The alkyl group may be linear or branched. "Branched" refers to an alkyl group in which a lower alkyl group, such as methyl, ethyl or propyl, is attached to a linear alkyl chain. The alkyl group can include one or more points of unsaturation including, for example, carbon-carbon double bonds and carbon-carbon triple bonds. Exemplary alkyl groups include, for example, methyl, ethyl, i-propyl, n-butyl, t-butyl, n-pentyl, heptyl, octyl, nonyl, decyl, undecyl, dodecyl, tridecyl, tetradecyl, pentadecyl and hexadecyl. Preferred alkyl groups include the lower alkyl groups having 1 to about 4 carbon atoms and the higher alkyl groups having about 10 to about 16 carbon atoms. Exemplary alkyl groups which contain alkyl group substituents include hydroxylated alkyl groups, such as alkyl groups derived from glycerol, including, for example, 2,3-dihydroxyprop-1-yl.

"Alkylene", when used in conjunction with the term "diradical", refers to a bivalent aliphatic hydrocarbon group having from 1 to about 30 carbon atoms. When used in conjunction with the term "linking group", "alkylene" refers to a bi- or trivalent aliphatic hydrocarbon group having from 1 to about 30 carbons. The alkylene group may be straight, branched or cyclic. The alkylene group may be also optionally unsaturated and/or substituted with one or more "alkyl group substituents." There may be optionally inserted along the alkylene group one or more oxygen, sulphur or substituted or unsubstituted nitrogen atoms, wherein the nitrogen substituent is alkyl as previously described. Exemplary alkylene groups include methylene (—$CH_2$—), ethylene (—$CH_2CH_2$—), propylene (—$(CH_2)_3$—), prop-1,2,3-triyl (—$CH_2$—CH(—)—$CH_2$—), cyclohexylene (—$C_6H_{10}$—), —CH=CH—CH=CH—, —CH=CH—$CH_2$—, —$(CF_2)_n$($CH_2)_m$—, wherein n is an integer from about 1 to about 22 and m is an integer from 0 to about 22, —$(CH_2)_n$—N(R)—$(CH_2)_m$—, wherein each of m and n is independently an integer from 0 to about 30 and R is hydrogen or alkyl, methylenedioxy (—O—$CH_2$—O—) and ethylenedioxy (—O—$(CH_2)_2$—O—). It is preferred that the alkylene group has about 2 to about 3 carbon atoms.

The present invention is directed, in part, to stabilized compositions which are useful, for example, as contrast agents for diagnostic and/or therapeutic ultrasound. The compositions comprise, in combination with a gas and preferably in an aqueous carrier, a fluorinated amphiphilic compound. The fluorinated amphiphilic compounds, which are described in detail below, impart highly desirable properties to the compositions of the present invention. For example, it has been surprisingly and unexpectedly found that the fluorinated amphiphilic compounds are capable of stabilizing the present compositions, including preferred compositions which comprise vesicles. It has been found also that the present fluorinated amphiphilic compounds are capable of promoting the formation of vesicles, as well as improving the stability of the formed vesicles. In embodiments in which the vesicles comprise gas-filled and/or gaseous precursor-filled vesicles, the fluorinated amphiphilic compounds enable the vesicles to substantially retain the gas and/or gaseous precursor with minimal loss or leakage. This is surprising and unexpected and generally renders unnecessary the use of additional stabilizing materials, including, for example, surfactants, and stabilizing techniques, including, for example, crosslinking of the materials in the walls of the vesicles. As discussed above, such techniques are generally necessary in connection with contrast agents of the prior art. Moreover, the present fluorinated amphiphilic compounds are generally biocompatible and can be obtained with minimal effort and at minimal expense. Accordingly, the present invention is directed to simple and efficient methods for providing stabilized compositions, including vesicular compositions, for use as ultrasound contrast agents.

A variety of fluorinated amphiphilic compounds can be employed in the present compositions. Preferred fluorinated amphiphilic compounds are those which, when combined with a gas, tend to form stabilized compositions and/or vesicles. Preferred also are fluorinated amphiphilic compounds which are capable of stabilizing the vesicles, once formed.

In preferred embodiments, the fluorinated amphiphilic compounds are based on amphiphilic compounds, including lipids, and especially phospholipids, which comprise a polar head group including, for example, a phosphorylated head group, such as a phosphatidylcholine group, or a sulfated head group, and at least one nonpolar aliphatic chain, such as a palmitoyl group. In such embodiments, the fluorine atoms are preferably substituted on the nonpolar aliphatic chain portions of the involved amphiphilic compounds. As noted above, among the preferred amphiphilic compounds are phosphorylated and/or sulfated lipid compounds. It is contemplated that the term "phosphorylate", as used herein, encompasses phosphate groups with various valences, including, for example, $PO_3$ and $PO_4$ groups. Similarly, it is contemplated that the term "sulfated", as used herein, encompasses sulfate groups with various valences, including, for example, $SO_3$ and $SO_4$. It is contemplated that in these preferred lipid compounds, the phosphate group and/or the sulfate group are preferably located within the backbone portions of the lipid compounds. Thus, generally speaking, the phosphate and/or sulfate groups in the preferred phosphorylated and/or sulfated lipid compounds are desirably spaced from the end-portions of the compounds with, for example, alkyl groups, and as such, are referred to herein as "internal phosphate (and/or sulfate) groups". These preferred fluorinated amphiphilic compounds can be contrasted with prior art fluorinated compounds, including, for example, the class of compounds which are commercially available as ZONYL™ fluorosurfactants (DuPont Chemical Corp., Wilmington Del.), including the ZONYL™ phosphate salts and the ZONYL™ sulfate salts, which have terminal phosphate or sulfate groups. Representatives of these salts are disclosed, for example, in U.S. Pat. No. 5,276,146, wherein the ZONYL™ phosphate salt has the formula $[F(CF_2CF_2)_{3-8}CH_2CH_2O]_{1,2}P(O)(O^-NH_4^+)_{2,1}$ and the ZONYL™ sulfate salt has the formula $F(CF_2CF_2)_{3-8}CH_2CH_2SCH_2CH_2N^+(CH_3)_3{}^{-OSO}{}_2OCH_3$. In contrast to the preferred phosphorylated and sulfated lipid compounds involved in the present invention, the ZONYL™ phosphate and sulfate salts, as depicted above, include phosphate and sulfate moieties in the terminal portions of the disclosed compounds.

In certain preferred embodiments, the fluorinated amphiphilic compounds are polyfluorinated. As noted above, this means that the amphiphilic compounds are preferably substituted with at least two or more fluorine atoms. In even more preferred embodiments, the fluorinated amphiphilic compounds are perfluorinated.

As noted above, preferred amphiphilic compounds on which the fluorinated amphiphiles are based, generally comprise at least one nonpolar aliphatic chain. In certain preferred embodiments, the amphiphilic compounds comprise, at most, one nonpolar aliphatic chain. Such compounds are referred to herein as "monochain compounds." In certain other preferred embodiments, the amphiphilic compounds comprise more than one, and preferably at least two or three, nonpolar aliphatic chains. Such compounds are referred to herein as "polychain compounds." Whether monochain or polychain, it is preferred that the fluorine atoms are substituted on the chain portion(s) of the amphiphilic compounds. The extent of the fluorination of the chain(s), and the location of the fluorine atoms on the chain(s), can be selected, as desired, in the fluorinated amphiphilic compounds. For example, only a certain portion of the nonpolar chain group, such as the terminal methyl group ($CH_3$—) or an internal methylene group (—$CH_2$—), can be fluorinated, with the remainder of the nonpolar chain group being, for example, unsubstituted aliphatic, such as unsubstituted alkyl. Alternatively, it is contemplated that a substantial majority of the nonpolar chain group can be fluorinated. The nonpolar chain group can include substantially equivalent portions which are fluorinated and nonfluorinated, as determined, for example, by the number of carbon atoms in the fluorinated and nonfluorinated portions. In preferred form, the nonpolar chain group contains both a nonfluorinated portion and a fluorinated portion.

With particular reference to polychain compounds, it is contemplated that all of the chains can be fluorinated, or only certain of the chains can be fluorinated. In the latter case, the nonfluorinated chain(s) can be, for example, unsubstituted aliphatic, including unsubstituted alkyl. Such compounds are referred to herein as "asymmetric amphiphilic compounds", since both fluorinated and nonfluorinated chains are present in the same molecule.

In connection with the preferred embodiments of the present invention involving mono- and polychain amphiphilic compounds, the nonpolar aliphatic chains can be referred to as having a proximal end portion and a distal end portion. The proximal end portion corresponds to that portion of the aliphatic chain which is proximate the polar head group. Thus, in the case of phospholipids, including, for example, phosphatidylcholines, such as mono- and dipalmitoylphosphatidylcholines, the proximal end portions of the palmitoyl moieties correspond to the portions of the chains which are located near the carbonyloxy (—C(=O)—O—) groups and the glycerolphosphocholine moiety. Similarly, the distal end portions correspond to the portions of the chains which are located near the terminal methyl groups of the alkyl chains of the palmitoyl moieties.

In preferred embodiments, at least the distal end portion of the nonpolar chain(s) of the mono- and polychain amphiphilic compounds is fluorinated, with polyfluorinated distal ends being more preferred. Even more preferably, the distal end portions of the nonpolar chains are perfluorinated.

Also in preferred embodiments, the proximal end portion of the nonpolar chain portion(s) are unsubstituted aliphatic, with unsubstituted alkyl being more preferred. Thus, particularly preferred embodiments of the invention involve fluorinated amphiphilic compounds in which one or more nonpolar aliphatic chains contain both a perfluorinated distal end portion and an unsubstituted proximal end portion.

In certain particularly preferred embodiments, the fluorinated amphiphilic compound has the formula

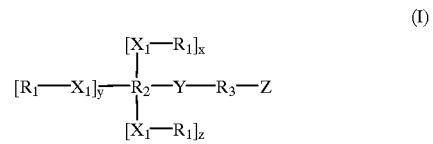

(I)

wherein:

each of x, y and z is independently 0 or 1;

each $X_1$ is independently —O—, —S—, —SO—, —$SO_2$—, —$NR_4$—, —C(=$X_2$)—, —C(=$X_2$)—O—, —O—C(=$X_2$)—, —C(=$X_2$)—$NR_4$— or —$NR_4$—C(=$X_2$)—;

$X_2$ is O or S;

Y is a direct bond or —$X_3$—M(=O)($OR_5$)$_q$—O—, where q is 1 or 2;

$X_3$ is a direct bond or —O—;

M is P or S;

Z is hydrogen, the residue of a hydrophilic polymer, a saccharide residue or —N($R_6$)$_r$, where r is 2 or 3;

each $R_1$ is independently alkyl of 1 to about 30 carbons or fluorinated alkyl of 1 to about 30 carbons;

$R_2$ is a direct bond or an alkylene linking group of 1 to about 10 carbons;

$R_3$ is a direct bond or an alkylene diradical of 1 to about 10 carbons;

each of $R_4$ and $R_5$ is independently hydrogen or alkyl of 1 to about 8 carbons; and each $R_6$ is independently hydrogen, alkyl of 1 to about 8 carbons or a residue of a hydrophilic polymer; provided that at least one of x, y and z is 1, at least one of $R_1$ is fluorinated alkyl of 1 to about 30 carbons, and when $R_2$ is a direct bond, two of x, y and z are each 0.

In the above formula (I), each of x, y and z is independently 0 or 1, provided that at least one of x, y and z is 1. In certain preferred embodiments, two of x, y and z are each 0. In certain other preferred embodiments, one of x, y and z is 0 or 1 and the other two of x, y and z are each 1, with one of x, y and z being 0 and the other two of x, y and z being 1 being more preferred. In certain other preferred embodiments, each of x, y and z is 1.

Each $X_1$ in formula (I) above is independently —O—, —S—, —SO—, —$SO_2$—, —$NR_4$—, —C(=$X_2$)—, —C(=$X_2$)—O—, —O—C(=$X_2$)—, —C(=$X_2$)—$NR_4$— or —$NR_4$—C(=$X_2$)—. Preferably, each $X_1$ is independently —O—, —S—, —C(=$X_2$)—, —C(=$X_2$)—O—, —O—C(=$X_2$)—, —C(=$X_2$)—$NR_4$— or —$NR_4$—C(=$X_2$)—. More preferably, each $X_1$ is independently —C(=$X_2$)—O— or —O—C(=$X_2$)—. Even more preferably, each $X_1$ is —C(=$X_2$)—O—.

In the above formula (I), each $X_2$ is O or S. Preferably, each $X_2$ is O.

In formula (I) above, Y is a direct bond or —$X_3$—M(=O)($OR_5$)$_q$—O—, where q is 1 or 2. Preferably, Y is —$X_3$—M(=O)($OR_5$)$_q$—O—.

M in the above definition of Y is P or S. Preferably, M is P.

$X_3$ in the above definition of Y is a direct bond or —O—. Preferably, $X_3$ is a direct bond.

In formula (I) above, Z is hydrogen, the residue of a hydrophilic polymer, a saccharide residue or —$N(R_6)_r$, where r is 2 or 3. In preferred embodiments, Z is —$N(R_6)_r$.

Each $R_1$ in formula (I) is independently alkyl of 1 to about 30 carbons or fluorinated alkyl of 1 to about 30 carbons, provided that at least one of $R_1$ is fluorinated alkyl of 1 to about 30 carbons. Thus, when only one of x, y and z is 1, $R_1$ is necessarily fluorinated alkyl of 1 to about 30 carbons. In certain preferred embodiments, where one or none of x, y and z is 0, and preferably where one of x, y and z is 0 and the other two of x, y and z are each 1, at least one of $R_1$ is alkyl of 1 to about 30 carbons and at least one of $R_1$ is fluorinated alkyl of 1 to about 30 carbons. In other preferred embodiments, each $R_1$ is independently fluorinated alkyl of 1 to about 30 carbons. When fluorinated alkyl of 1 to about 30 carbons, $R_1$ is preferably polyfluorinated alkyl of 1 to about 30 carbons, with perfluorinated alkyl of 1 to about 30 carbons being more preferred. When perfluorinated alkyl of 1 to about 30 carbons, $R_1$ is preferably $C_nF_{2n+1}$—$(CH_2)_m$—, where n is 1 to about 12 and m is 0 to about 18. In these latter embodiments, n is preferably about 2 to about 10 and m is preferably about 2 to about 14. More preferably, n is about 4 to about 8 and m is about 4 to about 10.

In formula (I) above, $R_2$ is a direct bond or an alkylene linking group of 1 to about 10 carbons, provided that when $R_2$ is a direct bond, two of x, y and z are each 0. Preferably, $R_2$ is a direct bond or an alkylene linking group of 1 to about 4 carbons. More preferably, $R_2$ is an alkylene linking group of about 3 carbons. Even more preferably, $R_2$ is —$CH_2$—CH(—)—$CH_2$—.

$R_3$ in formula (I) above is a direct bond or an alkylene diradical of 1 to about 10 carbons. Preferably, $R_3$ is a direct bond or an alkylene diradical of 1 to about 4 carbons. More preferably, $R_3$ is an alkylene diradical of about 2 carbons. Even more preferably, $R_3$ is —$CH_2CH_2$—.

In formula (I) above, each of $R_4$ and $R_5$ is independently hydrogen or alkyl of 1 to about 8 carbons. Preferably, each of $R_4$ and $R_5$ is independently hydrogen or alkyl of 1 to about 4 carbons. More preferably, each of $R_4$ and $R_5$ is hydrogen.

$R_6$ in formula (I) above is hydrogen, alkyl of 1 to about 8 carbons or a residue of a hydrophilic polymer. Preferably, $R_6$ is hydrogen or alkyl of 1 to about 4 carbons. More preferably, $R_6$ is hydrogen or methyl, with methyl being even more preferred.

In formula (I) above, it is intended that when any symbol appears more than once in a particular formula or substituent, its meaning in each instance is independent of the other. This independence of meaning is subject to any of the stated provisos.

Also in formula (I), it is intended that when each of two or more adjacent symbols is defined as being "a direct bond" to provide multiple, adjacent direct bonds, the multiple and adjacent direct bonds devolve into a single direct bond.

As noted above, Z and $R_6$ in the definition of Z in formula (I), can be, inter alia, the residue of a hydrophilic polymer. Exemplary polymers from which Z and/or $R_6$ can be derived include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates. The molecular weight of the polymers from which Z and/or $R_6$ are derived may vary, and is generally about 50 to about 5,000,000, with polymers having a molecular weight of about 100 to about 50,000 being preferred. More preferred polymers have a molecular weight of about 150 to about 10,000, with molecular weights of 200 to about 8,000 being even more preferred.

Preferred polymers from which Z and/or $R_6$ are derived include, for example, poly(ethyleneglycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred.

Other suitable hydrophilic polymers, in addition to those exemplified above, will be readily apparent to one skilled in the art based on the present disclosure. Generally, polymers from which Z and/or $R_6$ are derived include polymers that can be incorporated in the fluorinated amphiphilic compounds via alkylation or acylation reactions.

As with the various polymers exemplified above, it is contemplated that the polymeric residues can contain functional groups in addition, for example, to those typically involved in linking the polymeric residues to the fluorinated amphiphilic compounds. Such functionalities include, for example, carboxyl, amine, hydroxy and thiol groups. These functional groups on the polymeric residues can be further reacted, if desired, with materials which are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins and nucleosides.

In addition to residues of hydrophilic polymers, Z in formula (I) can also be a saccharide residue. Exemplary saccharides from which Z can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups.

Other suitable saccharides, in addition to those exemplified above, will be readily apparent to one skilled in the art based on the present disclosure. Generally, saccharides from which Z is derived include saccharides that can be incorporated in the fluorinated amphiphilic compounds via alkylation or acylation reactions.

A particularly preferred class of fluorinated amphiphilic compounds of the present invention, which are within the scope of the compound of formula (I), is represented by the formula

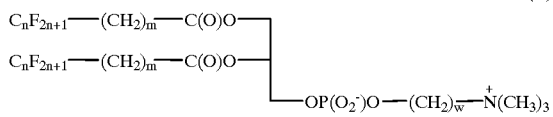

(II)

wherein:

m is 0 to about 18;

n is 1 to about 12; and w is 1 to about 8.

The integer m in formula (II) is 0 to about 18. Preferably, m is about 2 to about 14. More preferably, m is about 4 to about 10.

In formula (II) above, n is 1 to about 12. Preferably, n is about 2 to about 10, with about 4 to about 8 being more preferred.

The integer w in formula (II) is 1 to about 8. Preferably, w is 1 to about 4. More preferably, w is about 2.

The fluorinated amphiphilic compounds of the compositions of the present invention, including the compounds of formulas (I) and (II), can be prepared readily using standard organic synthetic methodology well known to those of ordinary skill in the art. Suitable methods for preparing fluorinated amphiphilic compounds are disclosed, for example, in C. Santaella et al., *New Journal of Chemistry,* 15, 685 (1991), the disclosures of which are hereby incorporated by reference, in their entirety. Exemplary of the available methods for preparing fluorinated amphiphilic compounds are synthetic methods based on the phosphorylation of 1,2-di-(F-alkylacyl)-3-glycerol derivatives. These methods can be utilized in the preparation of perfluoroalkyl phosphatidylcholines, and particularly perfluoroalkyl phosphatidylethanolamines, and are disclosed, for example, in the aforementioned Santaella publication. Such methods involve linear phosphorylating agents, including the Hirt and Berchtold reagent (2-bromoethyldichlorophosphate (BEDP)), which is readily available in large quantities. Hirt et al., *Pharm. Acta. Helv.,* 33, 349 (1958). BEDP is highly reactive and can be used to phosphorylate sterically hindered disubstituted glycerols. Hansen et al., *Lipids,* 17, 453 (1982). The ammonium group can be introduced by reaction of an appropriate amine with the 1,2-diacylglycero-3-(2-bromoethyl)phosphate intermediate to give the desired phosphatidylethanolamine derivatives. This synthetic methodology is depicted in the following reaction scheme.

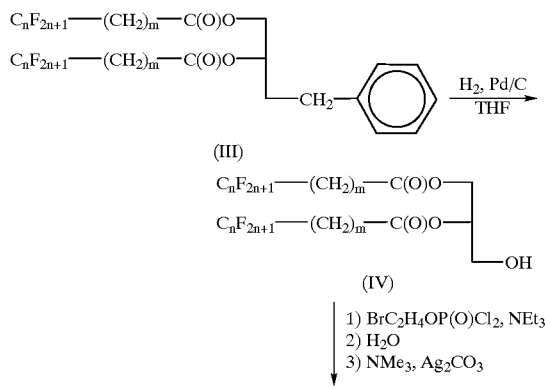

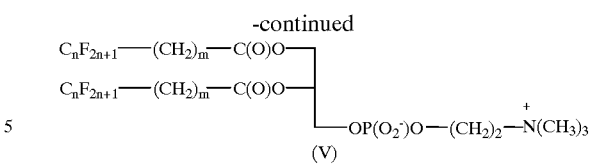

(V)

where m and n are as previously defined.

The 1,2-disubstituted-3-benzylglycerol derivatives of formula (III) are readily synthesized in high yields (85 to 90%) by acylation of 1-benzylglycerol with the corresponding perfluoroalkanoyl halides. *Proc. Natl. Acad. Sci. USA,* 75, 4074 (1978). The benzyl protecting group can be removed by hydrogenolysis over a palladium on charcoal catalyst (Pd/C) in tetrahydrofuran (THF). *Proc. Natl. Acad. Sci. USA,* 75, 4074 (1978). Short reaction times for the hydrogenolysis of the benzyl group are preferred to avoid transesterification of the 1,2-diacylglycerol of formula (III) into the more thermodynamically stable 1,3-diacylglycerol isomer. The hydrogenolysis reaction can be monitored by ordinary analytical techniques, including, for example, thin layer chromatography (TLC) and proton ($^1$H) nuclear magnetic resonance (NMR). The reaction is generally complete in about one hour with little or no transesterification. The hydrogenolysis reaction is preferably conducted in THF because both the starting material in the involved reaction (the compound of formula (III)) and the product (the compound of formula (IV)) tend to be highly soluble in THF. In addition, THF is conveniently used as the solvent in the subsequent phosphorylation step.

After hydrogenolysis, the catalyst (Pd/C) can be removed by filtration. The 1,2-diacylglycerols of formula (IV) can be reacted immediately with BEDP and an excess of triethylamine. Phosphorylation is typically completed in about 2 to about 4 hours, as measured by TLC. The remaining phosphochloride bond can be hydrolysed in aqueous base and generally requires about 22 hours for completion. When mineral bases or salts are used for hydrolysis including, for example, $Na_2CO_3$, KCl and EDTA sodium salt, the phosphate salts are highly insoluble in water or organic solvents. Fleischer, *Methods Enzymol.* 98, 263 (1983). The brominated intermediate can be isolated as a stable and soluble hydrogenotriethylammonium salt if excess triethylamine is used. Acidification of the phosphate salts to form the corresponding acid is difficult because the glycerol ester bonds are hydrolyzed at the necessary pH (pH of 2 to 3). Product degradation occurs also during purification over silica gel. Accordingly, it is preferred to use the phosphate salt without further purification. Nucleophilic displacement of the bromide ion by a large excess of trimethylamine occurs in a solvent mixture of $CHCl_3/CH_3CN$ at 45° C. over a 12 hour period. The displaced bromide ion can be precipitated by the addition of silver carbonate.

The concentration of fluorinated amphiphilic compound in the present compositions can vary and depends upon various factors, including, for example, the particular amphiphilic compound(s) which are employed in the compositions. Toxicity is generally of limited concern since the present fluorinated amphiphilic compounds are substantially biocompatible. See C. Santaella et al., *New Journal of Chemistry,* 15, 685 (1991). In general, the concentration of fluorinated amphiphilic compound in the present compositions is from about 0.001 mg/mL to about 200 mg/mL, with a concentration of about 0.01 mg/mL to 20 mg/mL being preferred. More preferably, the concentration of fluorinated amphiphilic compound is about 0.05 mg/mL to about 10 mg/mL, with a concentration of about 0.1 mg/mL to about 5 mg/mL being even more preferred.

The stabilized compositions of the present invention also comprise a gas, and preferably, an inert gas. The gases provide the compositions with enhanced reflectivity, particularly in vesicular composition in which the gas is entrapped within the vesicles. This increases their effectiveness as contrast agents.

Preferred gases are gases which are inert and which are biocompatible. Preferable gases include those selected from the group consisting of air, noble gases, such as helium, neon, argon and xenon, carbon dioxide, nitrogen, fluorine, oxygen, sulfur hexafluoride, fluorocarbons, perfluorocarbons, and mixtures thereof. Perfluorocarbons are preferred gases. Preferably, the perfluorocarbon is selected from the group consisting of perfluoromethane, perfluoroethane, perfluoropropane, perfluorobutane, perfluorocyclobutane and mixtures thereof. More preferably, the perfluorocarbon gas is selected from the group consisting of perfluoropropane and perfluorobutane, with perfluoropropane being particularly preferred. Another preferable gas is sulfur tetrafluoride.

It is contemplated that mixtures of different types of gases, including mixtures of a perfluorocarbon gas and another type of gas, such as air, can also be used in the compositions of the present invention. The gases discussed in Quay, International Application WO 93/05819, including the high "Q" factor gases described therein, may be used also. The disclosures of Quay, International Application WO 93/05819 are incorporated herein by reference in their entirety. In addition, paramagnetic gases and gases of isotopes, such as $^{17}O$, may be used. Other gases, including the gases exemplified above, would be readily apparent to one skilled in the art based on the present disclosure. The gases can be selected, as desired, to provide compositions which are suitable for use as contrast agents in ultrasound, as well as other diagnostic techniques, such as computed tomography (CT) and magnetic resonance imaging (MRI).

In certain preferred embodiments, a gas, for example, air or a perfluorocarbon gas, is combined with a liquid perfluorocarbon, such as perfluorohexane, perfluoroheptane, perfluorooctylbromide (PFOB), perfluorodecalin, perfluorododecalin, perfluorooctyliodide, perfluorotripropylamine and perfluorotributylamine.

It may also be desirable to incorporate in the stabilized compositions a precursor to a gaseous substance. Such precursors include materials that are capable of being converted to a gas in vivo. Preferably, the gaseous precursor is biocompatible, and the gas produced in vivo is biocompatible also.

A variety of gaseous precursors are available for use in the present compositions including, for example, substances which are sensitive to changes to pH. These substances include materials that are capable of evolving gas, for example, upon exposure to a pH that is substantially neutral or acidic. Examples of such pH sensitive substances include salts of an acid selected from the group consisting of inorganic acids, organic acids and mixtures thereof. Carbonic acid ($H_2CO_3$) is an example of a suitable inorganic acid, and aminomalonic acid is an example of a suitable organic acid. Other acids, including inorganic and organic acids, would be readily apparent to one skilled in the art based on the present disclosure.

Preferably, the gaseous precursor is a salt which is selected from the group consisting of an alkali metal salt, an ammonium salt and mixtures thereof. More preferably, the salt is selected from the group consisting of carbonate, bicarbonate, sesquecarbonate, aminomalonate and mixtures thereof.

Exemplary of gaseous precursor materials for use in the compositions of the present invention and which are salts include lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, Vol. 9, no. 3, pp. 525–532 (1970); Fitzpatrick et al., *Inorganic Chemistry*, Vol. 13, no. 3 pp. 568–574 (1974); and Stelmashok et al., *Koordinatsionnaya Khimiya*, Vol. 3, no. 4, pp. 524–527 (1977). The disclosures of these publications are hereby incorporated herein by reference.

In addition to, or instead of, being sensitive to changes in pH, the gaseous precursor materials may also comprise compounds which are sensitive to changes in temperature. Such temperature sensitive agents include, for example, materials which have a boiling point of greater than about 37° C. at atmospheric pressure. For example, perfluoropentane has a liquid/gas phase transition temperature (boiling point) of 29.5° C. at atmospheric pressure. This means that perfluoropentane will be a liquid at room temperature (about 25° C.), but will become a gas within the human body, the normal temperature of which is 37° C., which is above the transition temperature of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane is potentially useful as a gaseous precursor, although more likely as a gas, whereas perfluorohexane would likely be useful as a gaseous precursor because of its relatively high boiling point.

As discussed below, compositions containing gaseous precursors, such as perfluoropentane and/or perfluorohexane, can be prepared, for example, by agitating in a suitable container, such as a vial, an aqueous mixture of a fluorinated amphiphilic compound and a gaseous precursor at standard temperature and pressure. Under these conditions, the gaseous precursor would be in the form of a liquid. Alternatively, compositions containing gaseous precursors can be prepared at elevated temperature and atmospheric pressure in which case the gaseous precursor can be volatilized. Thus, for example, when a composition of a fluorinated amphiphile and perfluoropentane is prepared, for example, at a temperature of about 35° C. to about 40° C., the perfluoropentane is gaseous. The perfluoropentane would occupy the head space of the container in which the composition is prepared.

In addition to elevated temperature, amphiphilic compositions containing gaseous precursors can be prepared at about room temperature but at a reduced pressure. As known to those of ordinary skill in the art, the boiling point of various of the gaseous precursors described herein, including the perfluorocarbons, such as perfluoropentane and perfluorohexane, is lowered to about room temperature or less under reduced pressure. Thus, gaseous precursors can be incorporated into the present amphiphilic compositions as a gas by preparing the compositions at a reduced pressure. The volatilized gaseous precursor would then occupy the head space of the container in which the composition is prepared.

A wide variety of materials which are sensitive to changes in temperature can be used as gaseous precursors in the compositions of the present invention. Suitable gaseous precursors include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methylbutane, perfluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromo-butyraldehyde, carbonyl sulfide, crotononitrile, cyclobutane, methyl-cyclobutane, octafluorocyclobutane, perfluorocyclobutene, 3-chlorocyclopentene, perfluorocyclopentane, octafluorocyclopentene, cyclopropane, perfluorocyclopropane, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis-(dimethylphosphine)amine, perfluorohexane, perfluoroheptane, perfluorooctane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, perfluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neopentane, nitrous oxide, 1,2,3-nonadecane-tricarboxylic acid-2-hydroxytrimethylester, 1-nonene-3-yne, 1,4-pentadiene, n-pentane, perfluoropentane, 4-amino-4-methylpentan-2-one, 1-pentene, 2-pentene (cis), 2-pentene (trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-amino-propane, 2-chloropropane, heptafluoro-1-nitropropane, heptafluoro-1-nitrosopropane, perfluoropropane, propene, hexafluoropropane, 1,1,1,2,3,3-hexafluoro-2,3-dichloropropane, 1-chloropropane, chloropropane-(trans), 2-chloropropane, 3-fluoropropane, propyne, 3,3,3-trifluoropropyne, 3-fluorostyrene, sulfur (di)-decafluoride ($S_2F_{10}$), 2,4-diaminotoluene, trifluoroacetonitrile, trifluoromethyl peroxide, trifluoromethyl sulfide, tungsten hexafluoride, vinyl acetylene and vinyl ether. Examples of gaseous precursors are generally described, for example, in U.S. Pat. Nos. 5,088,499 and 5,149,319, the disclosures of which are hereby incorporated herein by reference in their entirety.

Perfluorocarbons are preferred gaseous precursors for use in the compositions of the present invention. Exemplary of perfluorocarbon gaseous precursors are perfluorocarbons selected from the group consisting of perfluoropentane, perfluorohexane, perfluoroheptane, perfluorooctane and perfluorononane. Preferably, the perfluorocarbon gaseous precursor is selected from the group consisting of perfluoropentane, perfluorohexane and perfluorooctane, with perfluoropentane being particularly preferred.

The gaseous precursor materials may be also photoactivated materials, such as diazonium ion and aminomalonate. As discussed more fully hereinafter, certain stabilized compositions, and particularly vesicular compositions, may be formulated so that gas is formed at the target tissue or by the action of sound on the particle. Other gaseous precursors, in addition to those exemplified above, will be apparent to one skilled in the art based on the present disclosure.

As noted above, certain preferred embodiments of the present invention involve vesicular compositions. The size of the vesicles can be adjusted, if desired, by a variety of procedures including, for example, microemulsification, vortexing, extrusion, filtration, sonication, homogenization, repeated cycles of freezing and thawing, extrusion under pressure through pores of defined size, and similar methods.

For intravascular use, the vesicles preferably have diameters of less than about 30 $\mu$m, and more preferably, less than about 12 $\mu$m. For targeted intravascular use including, for example, binding to certain tissue, such as cancerous tissue, the vesicles can be significantly smaller, for example, less than 100 nm in diameter. For enteric or gastrointestinal use, the vesicles can be significantly larger, for example, up to a millimeter in size. Preferably, the vesicles are sized to have diameters between about 20 $\mu$m and 100 $\mu$m.

Tabulated below is a listing of a series of gaseous precursors which undergo phase transitions from liquid to gas at relatively close to normal human body temperature (37° C.) or below. Also listed in the table are the sizes, in diameter, of emulsified droplets that would be required to form a vesicle of a maximum size of about 10 $\mu$m.

TABLE I

Physical Characteristics of Gaseous Precursors and Diameter of Emulsified Droplet to Form a 10 $\mu$m Vesicle

| Compound | Molecular Weight | Boiling Point (°C.) | Density | Diameter ($\mu$m) of emulsified droplet to make 10 micron vesicle |
|---|---|---|---|---|
| perfluoropentane | 288.04 | 29.5 | 1.7326 | 2.9 |
| 1-fluorobutane | 76.11 | 32.5 | 6.7789 | 1.2 |
| 2-methylbutane (isopentane) | 72.15 | 27.8 | 0.6201 | 2.6 |
| 2-methyl-1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |

TABLE I-continued

Physical Characteristics of Gaseous Precursors and
Diameter of Emulsified Droplet to Form a 10 μm Vesicle

| Compound | Molecular Weight | Boiling Point (°C.) | Density | Diameter (μm) of emulsified droplet to make 10 micron vesicle |
|---|---|---|---|---|
| octafluorocyclobutane | 200.04 | −5.8 | 1.48 | 2.8 |
| decafluorobutane | 238.04 | −2 | 1.517 | 3.0 |
| hexafluoroethane | 138.01 | −78.1 | 1.607 | 2.7 |

*Source: Chemical Rubber Company Handbook of Chemistry and Physics Robert C. Weast and David R. Lide, eds. CRC Press, Inc. Boca Raton, Fla. (1989–1990).

The utility of the compositions of the present invention can be optimized, for example, by using gases of limited solubility. Limited solubility, as used herein, refers to the ability of the gas to diffuse, for example, out of vesicles by virtue of its solubility in the surrounding aqueous medium. A greater solubility in the aqueous medium imposes a gradient with the gas in the vesicle such that the gas will have a tendency to diffuse out of the vesicle. A lesser solubility in the aqueous medium will decrease the gradient between the vesicle and the interface such that the diffusion of the gas out of the vesicle will be impeded. Preferably, the gas entrapped in the vesicle has a solubility less than that of oxygen, namely, 1 part gas in 32 parts water. See *Matheson Gas Data Book*, Matheson Company, Inc. (1966). More preferably, the gas entrapped in the vesicle possesses a solubility in water less than that of air; and even more preferably, the gas entrapped in the vesicle possesses a solubility in water less than that of nitrogen.

The gases and/or gaseous precursors are preferably incorporated in the stabilized compositions of the present invention irrespective of the physical nature of the composition. Thus, it is contemplated that the gases and/or precursors thereto are incorporated in compositions in which the fluorinated amphiphilic compounds are aggregated, for example, substantially randomly, as well as compositions in which the fluorinated amphiphilic compounds form vesicles, including micelles and liposomes. Incorporation of the gases and/or gaseous precursors in the present compositions may be achieved by using any of a number of methods. For example, the formation of gas-filled vesicles can be achieved by shaking or otherwise agitating an aqueous mixture which comprises a gas or gaseous precursor and the fluorinated amphiphilic compounds. This promotes the formation of stabilized vesicles within which the gas or gaseous precursor is encapsulated.

In addition, a gas may be bubbled directly into an aqueous mixture of the fluorinated amphiphilic compounds. Alternatively, a gas instillation method can be used as disclosed, for example, in U.S. Pat. Nos. 5,352,435 and 5,228,446, the disclosures of each of which are hereby incorporated herein by reference in their entirety. Suitable methods for incorporating the gas or gaseous precursor in the present compositions are disclosed also in U.S. Pat. No. 4,865,836, the disclosures of which are hereby incorporated herein by reference. Other methods would be apparent to one skilled in the art based on the present disclosure.

In preferred embodiments, the gases and/or gaseous precursor materials are incorporated in vesicular compositions, with micelles and liposomes being preferred. As discussed in detail below, vesicles in which a gas or gas precursor or both are encapsulated are advantageous in that they provide improved reflectivity in vivo.

In certain embodiments, the stabilized compositions of the present invention can further comprise one or more additional amphiphilic materials. Due to the amphipathy of these additional amphiphilic materials, they are generally capable, in preferred form, of enhancing or otherwise improving the stability of the present compositions. It has been found that incorporating one or more additional amphiphilic materials is particularly advantageous in connection with compositions involving asymmetric fluorinated amphiphilic compounds. Particularly preferred additional amphiphilic materials include compounds which are biocompatible and which are capable of promoting the formation of vesicles, and especially stabilized vesicles, in the present stabilized compositions.

In certain preferred embodiments, the additional amphiphilic materials comprise a lipid compound. Suitable amphiphilic materials comprise a lipid compound. Suitable lipids include, for example, phospholipids, such as phosphatidylcholine with both saturated and unsaturated fatty acids, including dioleoylphosphatidylcholine, dimyristoylphosphatidylcholine, dipalmitoylphosphatidylcholine and distearoylphosphatidylcholine; phosphatidylethanolamines, such as dipalmitoylphosphatidylethanolamine, dioleoylphosphatidylethanolamine, N-succinyldioleoylphosphatidylethanolamine and 1-hexadecyl-2-palmitoylglycerophosphoethanolamine; phosphatidylserine; phosphatidylglycerol; sphingolipids; glycolipids, such as ganglioside GM1; glucolipids; sulfatides; glycosphingolipids; phosphatidic acids, such as dipalmitolylphosphatidic acid; palmitic acid; stearic acid; arachidonic acid; oleic acid; lipids bearing polymers, such as polyethyleneglycol or polyvinylpyrrolidone; cholesterol and cholesterol hemisuccinate; 12-(((7'-diethylaminocoumarin-3-yl)carbonyl)methylamino)octadecanoic acid; N-[12-(((7'-diethylaminocoumarin-3-yl)carbonyl)methylamino) octadecanoyl]-2-aminopalmitic acid; cholesteryl-(4'-trimethylamino)butanoate; 1,2-dioleoyl-sn-glycerol; 1,2-dipalmitoyl-sn-3-succinylglycerol; 1,3-dipalmitoyl-2-succinylglycerol; and palmitoylhomocysteine.

Suitable additional amphiphilic materials include also lipid compounds used to make mixed micelle systems, such as laurytrimethylammonium bromide; cetyltrimethylammonium bromide; myristyltrimetheylammonium bromide; alkyldimethylbenzylammonium chloride (where alkyl is, for example, $C_{12}$, $C_{14}$ or $C_{15}$); benzyldimethyldodecylammonium bromide/chloride; benzyldimethylhexadecylammonium bromide/chloride; benzyldimethyltetradecylammonium bromide/chloride; cetyldimethylethylammonium bromide/chloride; and cetylpyridinium bromide/chloride.

Suitable additional amphiphilic materials for use in the present compositions include also lipid compounds carrying a net charge, for example, anionic and/or cationic lipids. Exemplary cationic lipids include, for example, N-[1-(2,3-dioleoyloxy)propyl]-N,N,N-trimethylammonium chloride) (DOTMA), dioleoyloxy-3-(trimethylammonium)propane) (DOTPA) and 1,2,-dioleoyloxy-e-(4'-trimethylammonium) butanoyl-sn-glycerol.

In addition to, or instead of, the lipid compounds described above, the additional amphiphilic materials may comprise aliphatic carboxylic acids, for example, fatty acids. Preferred fatty acids include those which contain about 5 to about 22 carbon atoms in the aliphatic group. The aliphatic group can be either linear or branched. Exemplary saturated fatty acids include, for example, (iso)lauric, (iso)myristic, (iso)palmitic and (iso)stearic acids. Exemplary unsaturated fatty acids include, for example, lauroleic, physeteric, myristoleic, palmitoleic, petroselinic, and oleic acid. Suitable fatty acids include also, for example, fatty acids in which the aliphatic group is an isoprenoid or prenyl group.

The present compositions can also comprise, if desired, one or more neutral or positively or negatively charged materials. Exemplary neutral materials include, for example, oils, such as peanut oil, canola oil, olive oil, safflower oil and corn oil; lecithin; sphingomyelin; cholesterol and derivatives thereof; squalene; terpenes and terpenoid compounds; triglycerides; gums, such as xanthan, tragacanth, locust bean, guar and carrageenan gums; methoxylated pectin; starch; agarose; cellulose and semi-synthetic cellulose, for example, methyl cellulose, hydroxyethyl cellulose, methoxy cellulose and hydroxypropyl cellulose; nonionic materials, including, for example, polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylenepolyoxypropylene polymers and polyoxyethylene fatty acid stearates; acacia; agar; bentonites, including purified bentonite; magma; carbomer 934P; dextrin; gelatin; di- and trihydroxy substituted alkanes and their polymers, including polyvinylalcohol; mono-, di- and triglycerides; amino alcohols; monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose.

Suitable positively charged materials include compounds containing, for example, protonated or quaternary amino groups, including polymers in which the repeating units contain one or more amino groups, such as peptides, polypeptides, proteins and lipoproteins, such as albumin and natural lipoproteins. Exemplary positively charged materials include, for example, chitin; alkanolamines, such as monoethanolamine, diethanolamine and triethanolamine, and mixtures thereof, including, for example, trolamine; polylysine; polyarginine; polyethyleneimine; chitosan; and peptides, including melanin concentrating hormone and dynorphin. Suitable negatively charged materials are compounds containing, for example, carboxy ($CO_2^-$) groups, including polycarboxy polymers. Exemplary negatively charged materials include, for example, carboxymethylcellulose; salts of alginic acid, such as sodium and calcium alginate; salts of glycosaminoglycans, including salts of hyaluronic acid; phosphorylated and sulfonated derivatives of carbohydrates; genetic material, such as interleukin-2 and interferon; phosphorothioate oligomers; and negatively charged peptides, such as deltorphin. In addition, carbohydrates bearing polymers may be used in the present compositions. Carbohydrate bearing lipids are described, for example, in U.S. Pat. No. 4,310,505, the disclosures of which are hereby incorporated by reference herein, in their entirety.

In certain circumstances, it may be desirable to incorporate one or more charged species into the present amphiphilic compositions. It is believed that such charged species can contribute to the stability of the present amphiphilic compositions. Examples of suitable charged species include, for example, cations, such as metal ions, or anions. Exemplary cations include, for example, calcium, manganese, magnesium, copper, gadolinium or dysprosium cations, or any other cation which is compatible for use in connection with pharmaceutical applications. Suitable anions include, for example, sulphur, peroxides or superoxides. The anionic species may be chelated with chelating agents, for example, ethylenediaminetetraacetic acid (EDTA) and diethylenetriaminepentaacetic acid (DTPA).

Other materials which can be incorporated in the present compositions and which are contemplated as being capable of improving the stability of the compositions include polymeric materials. Exemplary of such polymeric materials include, for example, the polymers from which Z and/or $R_6$ in formula (I) are derived, as discussed hereinbefore.

It may be desirable to include in the amphiphilic compositions of the present invention anti-bactericidal agents and/or preservatives. Examples of these materials include, for example, sodium benzoate, quaternary ammonium salts, sodium azide, methyl paraben, propyl paraben, sorbic acid, ascorbyl, palmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulphur dioxide and organic mercurial salts.

Other additional materials which can be incorporated in the present compositions would be apparent to one skilled in the art based on the present disclosure. Preferably, the additional materials are selected to optimize certain desirable properties of the compositions, including serum stability and plasma half-life. This can be achieved without undue experimentation, based on the present disclosure.

The concentration of the additional materials in the present compositions can vary and depends, for example, upon the particular fluorinated amphiphilic compounds which are employed. In preferred embodiments, the concentration of additional materials is from about 0.01 mg/mL to about 200 mg/mL. More preferably, the concentration of additional materials is from about 0.05 mg/mL to about 5 mg/mL, with concentrations of about 15 mg/mL to about 2.5 mg/mL being even more preferred.

In certain preferred embodiments of the invention, the stabilized compositions comprise a vesicular composition. The vesicular compositions may comprise micelles and/or liposomes. A wide variety of methods are available for the preparation of vesicular compositions, including, for example, shaking, drying, gas-installation, spray drying, and the like. Suitable methods for preparing the vesicular compositions are described, for example, in U.S. application Ser. No. 307,305, filed Sep. 16, 1994, the disclosures of which are incorporated herein by reference.

In preferred embodiments, fluorinated amphiphilic compounds are used in the preparation of the present compositions, including vesicular compositions, which are in the gel state at physiological temperature. As known to one of ordinary skill in the art, the main phase transition temperature ($T_c$) of nonfluorinated amphiphilic compounds, such as lipids, including, for example, phosphatidylcholines, is based generally on the length of the carbon chains which are linked to the glycerol moiety. Exemplary representative lipids and their phase transition temperatures are set forth in the following table.

TABLE II

Saturated Diacyl-sn-Glycero-3-Phosphocholines:
Main Chain Melting Transition Temperatures

| Number of Carbons in Acyl Chains | Main Phase Transition Temperature (°C.) |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, for example, Derek Marsh, *CRC Handbook of Lipid Bilayers*, p. 139 (CRC Press, Boca Raton, Fla. 1990).

With respect to the fluorinated amphiphiles involved in the present invention, it is believed that the number of carbon atoms which are fluorinated has a greater effect on $T_c$, as opposed to the length of the chain(s), generally. In general, the greater the number of carbons fluorinated in one or more of the chains, the higher the $T_c$. Main chain transition temperatures of the compound of formula (V), which is the product in the foregoing reaction scheme and which is depicted below, are set forth in the following table.

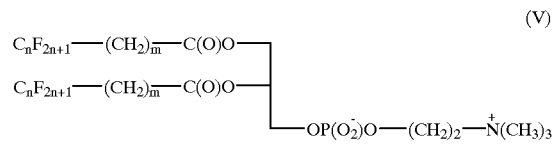

(V)

TABLE III

Perflourinated Diacyl-sn-Glycero-3-Phosphocholines:
Main Chain Melting Transition Temperatures

| Compound (V) | m | n | Main Phase Transition Temperature (°C.) |
|---|---|---|---|
| (A) | 4 | 4 | a* |
| (B) | 4 | 6 | a* |
| (C) | 4 | 8 | 69.3 |
| (D) | 10 | 4 | 18.6 |
| (E) | 10 | 6 | 56.4 |
| (F) | 10 | 8 | >95 |

An asterisk (*) means that no transition was detected between temperatures of 4° C. and 95° C.

With particular reference to the preparation of micelle compositions, the following discussion is provided. Micelles may be prepared using any one of a variety of conventional micellar preparatory methods which will be apparent to those skilled in the art. These methods typically involve suspension of the fluorinated amphiphilic compound and additional amphiphilic compound, as desired, in an organic solvent, evaporation of the solvent, resuspension in an aqueous medium, sonication and centrifugation. The foregoing methods, as well as others, are discussed, for example, in Canfield et al., *Methods in Enzymology*, Vol. 189, pp. 418–422 (1990); El-Gorab et al, *Biochem. Biophys. Acta*, Vol. 306, pp. 58–66 (1973); *Colloidal Surfactant*, Shinoda, K., Nakagana, Tamamushi and Isejura, Academic Press, New York (1963) (especially "The Formation of Micelles", Shinoda, Chapter 1, pp. 1–88); *Catalysis in Micellar and Macromolecular Systems*, Fendler and Fendler, Academic Press, New York (1975). The disclosures of each of the foregoing publications are incorporated by reference herein, in their entirety.

The vesicular composition may also comprise liposomes. In any given liposome, the involved amphiphilic compound (s), including fluorinated and nonfluorinated amphiphilic compound, may be in the form of a monolayer or bilayer, and the mono- or bilayers may be used to form one or more mono- or bilayers. In the case of more than one mono- or bilayer, the mono- or bilayers are generally concentric. Thus, the amphiphilic compounds may be used to form unilamellar liposomes (comprised of one monolayer or bilayer), oligo-lamellar liposomes (comprised of two or three monolayers or bilayers) or multilamellar liposomes (comprised of more than three monolayers or bilayers).

A wide variety of methods are available in connection with the preparation of liposome compositions. Accordingly, the liposomes may be prepared using any one of a variety of conventional liposomal preparatory techniques which will be apparent to those skilled in the art. These techniques include solvent dialysis, French press, extrusion (with or without freeze-thaw), reverse phase evaporation, micro-emulsification and simple freeze-thawing. The liposomes may also be prepared by various processes which involve shaking or vortexing. This may be achieved, for example, by the use of a mechanical shaking device, such as a Wig-L-Bug™ (Crescent Dental, Lyons, Ill.). Conventional micro-emulsification equipment, such as a Microfluidizer™ (Microfluidics, Woburn, Mass.) may be used also.

Additional methods for the preparation of liposome compositions include, for example, sonication, chelate dialysis, homogenization, solvent infusion, spontaneous formation, solvent vaporization, controlled detergent dialysis, and others, each involving the preparation of liposomes in various fashions. Methods which involve freeze-thaw techniques are preferred in connection with the preparation of liposomes. Suitable freeze-thaw techniques are described, for example, in copending U.S. application Ser. No. 07/838,504, filed Feb. 19, 1992, the disclosures of which are incorporated herein by reference in their entirety. Preparation of the liposomes may be carried out in a solution, such as an aqueous saline solution, aqueous phosphate buffer solution, or sterile water.

As noted above, the size of the vesicles, including liposomes, can be adjusted, if desired, by a variety of techniques, including extrusion, filtration, sonication and homogenization. In addition, the size of the liposomes can be adjusted by the introduction of a laminar stream of a core of liquid into an immiscible sheath of liquid. Other methods for adjusting the size of the liposomes and for modulating the resultant liposomal biodistribution and clearance of the liposomes would be apparent to one skilled in the art based on the present disclosure. Preferably, the size of the liposomes is adjusted by extrusion under pressure through pores of a defined size. Although liposomes employed in the subject invention may be of any one of a variety of sizes, the liposomes are preferably small, that is, less than about 100 nanometer (nm) in outside diameter.

Many of the foregoing liposomal preparatory techniques, as well as others, are discussed, for example, in U.S. Pat. No. 4,728,578; U.K. Patent Application GB 2193095 A; U.S. Pat. No. 4,728,575; U.S. Pat. No. 4,737,323; International Application Serial No. PCT/US85/01161; Mayer et al., *Biochimica et Biophysica Acta*, Vol. 858, pp. 161–168 (1986); Hope et al., *Biochimica et Biophysica Acta*, Vol. 812, pp. 55–65 (1985); U.S. Pat. No. 4,533,254; Mayhew et al., *Methods in Enzymology*, Vol. 149, pp. 64–77 (1987); Mayhew et al., *Biochimica et Biophysica Acta*, Vol 755, pp. 169–74 (1984); Cheng et al, *Investigative Radiology*, Vol. 22, pp. 47–55 (1987); International Application Serial No. PCT/US89/05040; U.S. Pat. No. 4,162,282; U.S. Pat. No. 4,310,505; U.S. Pat. No. 4,921,706; and *Liposome Technology*, Gregoriadis, G., ed., Vol. I, pp. 29–31, 51–67 and 79–108 (CRC Press Inc., Boca Raton, Fla. 1984), the disclosures of each of which are hereby incorporated by reference herein, in their entirety.

Although any of a number of varying techniques can be used, it is contemplated that the vesicular compositions of the present invention are preferably prepared using a shaking technique. Preferably, the shaking technique involves agitation with a mechanical shaking apparatus, such as a Wig-L-Bug™ (Crescent Dental, Lyons, Ill.), such as those disclosed in copending U.S. application Ser. No. 160,232, filed Nov. 30, 1993, the disclosures of which are hereby incorporated herein by reference in their entirety.

In certain embodiments of the present invention, the compositions further comprise a bioactive agent. These compositions are referred to herein as "amphiphilic formulations", and can be used for the therapeutic delivery in vivo of bioactive agents. Preferably, the amphiphilic formulations comprise vesicular formulations. In vesicular formulations, circulation and delivery of the vesicles to the targeted tissue can be observed via a non-invasive procedure. In connection with gas-filled or gaseous precursor-filled vesicles, the application of high energy ultrasound, radio frequency, optical energy, for example, laser light, and/or heat, to produce areas of hyperthermia, can be used, if desired, to rupture the vesicles in vivo and thereby promote release of the entrapped gas and/or gaseous precursor and bioactive agent. Thus, vesicular formulations permit the controlled release of a bioactive agent in vivo.

As those skilled in the art will recognize, any of the present stabilized compositions and/or formulations may be lyophilized for storage, and reconstituted, for example, with an aqueous medium (such as sterile water or phosphate buffered solution, or aqueous saline solution), with the aid of vigorous agitation. To prevent agglutination or fusion of the fluorinated amphiphilic compounds and/or additional amphiphilic compounds as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

In the case of vesicular compositions, including micelles and liposomes, it is contemplated that the bioactive agent is preferably entrapped within a void of the vesicles. In certain cases, the bioactive agent can be incorporated also into the membrane walls of the vesicle. In the case of amphiphilic compositions in which the amphiphilic compounds are substantially aggregated randomly, or substantially not aggregated, it is contemplated that the bioactive agent is generally dispersed homogeneously throughout the composition.

The bioactive agent which is incorporated in the present compositions is preferably a substance which is capable of exerting a therapeutic biological effect in vitro and/or in vivo. Pharmaceuticals, drugs and genetic material are examples of suitable bioactive agents. Examples of genetic materials include, for example, genes carried on expression vectors, such as plasmids, phagemids, cosmids, yeast artificial chromosomes (YACs) and defective- or "helper" viruses; anti-sense and sense oligonucleotides; phosphorothioate oligodeoxynucleotides; antigene nucleic acids; and single and double stranded RNA and DNA, including DNA which encodes at least a portion of a gene, for example, DNA which encodes for human leukocyte antigen (HLA), dystrophin, cystic fibrosis transmembrane receptor (CFTR), interleukin-2 (IL-2), tumor necrosis factor (TNF) and granulocyte-macrophage colony stimulating factor (GMCSF). The DNA can also encode certain proteins which may be used in the treatment of various types of pathologies or conditions, including those which are associated with the loss or deterioration of immune competence. Such pathologies or conditions involving immune competence include, for example, acquired immune deficiency syndrome (AIDS), cancer, chronic viral infections, and autoimmune disease.

Specifically, DNA may be selected which expresses adenosine deaminase (ADA) for the treatment of ADA deficiency; growth hormone for the treatment of growth deficiency or to aid in the healing of tissues; insulin for the treatment of diabetes; luteinizing hormone releasing hormone (LHRH) antagonist as a birth control agent; LHRH for the treatment of prostate or breast cancer; tumor necrosis factor and/or interleukin-2 for the treatment of advanced cancers; high-density lipoprotein (HDL) receptor for the treatment of liver disease; thymidine kinase for the treatment of ovarian cancer, brain tumors, or human immunodeficiency virus (HIV) infection; HLA-B7 for the treatment of malignant melanoma; IL-2 for the treatment of neuroblastoma, malignant melanoma or kidney cancer; interleukin-4 (IL-4) for the treatment of cancer; HIV env for the treatment of HIV infection; antisense ras/p53 for the treatment of lung cancer; and Factor VIII for the treatment of Hemophilia B. Such therapies are described, for example, in *Science*, Vol. 258, pp. 744–746 (1992), the disclosure of which is incorporated herein by reference in its entirety.

In certain embodiments, it is desirable to incorporate in the amphiphilic compositions materials which comprise, for example, a polymer, such as an alginic acid polymer, that is covalently linked to a bioactive agent. An example of such a material is nalidixic acid alginate in which a polymer (alginic acid) is covalently linked to a bioactive material (nalidixic acid). Such materials are desirable in that it is believed they are capable of improving and/or enhancing the stability of the amphiphilic compositions, as well as providing a source of bioactive agent. It is contemplated also that after administration, the materials are hydrolyzed in vivo, to bioactive agent (nalidixic acid) and polymer (alginic acid).

As with the stabilized amphiphilic compositions, a wide variety of techniques also exist for the preparation of stabilized amphiphilic formulations. For example, the formulations may be prepared from a mixture of amphiphilic compounds, bioactive agent and gas or gaseous precursor. In this case, stabilized compositions are prepared as described above in the presence of a bioactive agent. Thus, for example, micelles and liposomes can be prepared in the presence of a bioactive agent. The preparation can involve, for example, bubbling a gas directly into an aqueous mixture of the fluorinated amphiphilic compounds and additional amphiphilic materials, as desired, and bioactive agent. Alternatively, the amphiphilic compositions may be preformed from fluorinated amphiphilic compounds and gas or gaseous precursor. In the latter case, the bioactive agent is then added to the amphiphilic composition prior to use. For example, an aqueous mixture of liposomes and gas may be prepared to which the bioactive agent is added and which is agitated to provide the liposome formulation. The liposome formulation is readily isolated also in that the gas- and/or bioactive agent-filled liposome vesicles generally float to the top of the aqueous solution. Excess bioactive agent can be recovered from the remaining aqueous solution.

The present amphiphilic compositions and/or formulations are suitable for diagnostic and/or therapeutic applications. In the case of diagnostic applications, such as ultrasound, the amphiphilic compositions, which may further comprise a gaseous precursor, are administered to a patient. Energy, preferably in the form of ultrasonic energy, is applied to at least a portion of the patient to image a region, which may include targeted tissue. A visible image of an internal region of the patient is then obtained, such that the presence or absence of diseased tissue can be ascertained.

Ultrasonic imaging techniques, including second harmonic imaging, are well known in the art, and are described, for example, in Uhlendorf, "Physics of Ultrasound Contrast Imaging: Scattering in the Linear Range", *IEEE Transactions on Ultrasonics, Ferroelectrics, and Frequency Control*, Vol. 14(1), pp. 70–79 (1994) and Sutherland, et al., "Color Doppler Myocardial Imaging: A New Technique for the Assessment of Myocardial Function", *Journal of the American Society of Echocardiography*, Vol. 7(5), pp. 441–458 (1994), the disclosures of which are hereby incorporated herein by reference in their entirety.

With respect to therapeutic applications, the present amphiphilic formulations can be used in either in vitro or in vivo applications. In the case of in vitro applications, including cell culture applications, the amphiphilic formulations can be added to the cells in cultures and then incubated. If desired, where liposomes are employed, energy, such as sonic energy, may be applied to the culture media to burst the liposomes and release any therapeutic agents.

With respect to in vivo applications, the formulations of the present invention can be administered to a patient in a variety of forms adapted to the chosen route of administration, including, for example, parenteral, oral, or intraperitoneal. Parenteral administration, which is preferred, includes administration by the following routes: intravenous; intramuscular; interstitially; intra-arterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration.

After vesicular formulations which comprise a gas and bioactive agent and, optionally, a gaseous precursor, have been administered to a patient, energy, preferably in the form of ultrasonic energy, can be applied to the target tissue to identify the location of the vesicles. The applied energy may also be employed to effect release of the bioactive agent and to facilitate cellular uptake of the bioactive agent. As one skilled in the art would recognize, based on the present disclosure, this method of mediating cellular uptake of bioactive agents with ultrasonic energy is preferably effected with tissues whose acoustic window permits the transmission of ultrasonic energy. This is the case for most tissues in the body, including, for example, muscle and organ tissues, such as the heart and liver, as well as most other vital structures. With respect to brain tissue, it may be necessary to create a "surgical window" by removing part of the skull, inasmuch as ultrasonic energy generally does not transmit through bone. Intravascular and/or endoluminal ultrasound transducers may be used to apply the ultrasound energy to selected tissues and/or sites in the body, for example, the aorta and the esophagus.

Fluorinated amphiphilic formulations can be formulated to be sufficiently stable in the vasculature such that they circulate throughout the body and provide blood pool equilibration. As one skilled in the art would recognize, based on the present disclosure, the formulations, including those which comprise suspensions, emulsions and/or vesicles, such as liposomes and micelles, may be coated with certain materials to minimize uptake by the reticuloendothelial system. Suitable coatings include, for example, gangliosides and glycolipids which bind saccharide moieties, such as glucuronate, galacturonate, guluronate, poly(ethylene glycol), poly(propylene glycol), polyvinylpyrrolidone, poly (vinyl alcohol), dextran, starch, phosphorylated and sulfonated mono-, di-, tri-, oligo- and polysaccharides and albumin. Provided that the circulation half-life of the formulations is of a sufficient period of time, they will generally pass through the target tissue while passing through the body. In the case of formulations which comprise a bioactive agent, energy, for example, sonic energy, may be focused on the tissue to be treated, for example, diseased tissue. The bioactive agent will then be released locally in the target tissue. The inventors have found also that antibodies, carbohydrates, peptides, glycopeptides, glycolipids and lectins also assist in the targeting of tissue. Accordingly, these materials may be incorporated into the fluorinated amphiphilic formulations also.

Different levels of energy are generally associated with diagnostic and therapeutic ultrasound. For example, the levels of energy associated with diagnostic ultrasound are generally insufficient to cause rupture of vesicles and/or to facilitate release and cellular uptake of the bioactive agents. Moreover, diagnostic ultrasound involves the application of one or more pulses of sound. Pauses between pulses permits the reflected sonic signals to be received and analyzed. The limited number of pulses used in diagnostic ultrasound limits the effective energy which is delivered to the tissue that is being studied.

On the other hand, higher energy ultrasound, for example, ultrasound which is generated by therapeutic ultrasound equipment, is generally capable of causing rupture of the vesicles. In general, therapeutic ultrasound machines use from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may be pulsed also. If pulsed sound energy is used, the sound will generally be pulsed in echo train lengths of about 8 to about 20 or more pulses at a time. Preferably, the echo train lengths are about 20 pulses at a time. In addition, the frequency of the sound used may vary from about 0.25 to about 100 megahertz (MHz). In general, frequency for therapeutic ultrasound ranges between about 0.75 and about 3 MHz are preferred with about 1 and about 2 MHz being more preferred. In addition, energy levels may vary from about 0.5 Watt (W) per square centimeter (cm$^2$) to about 5.0 W/cm$^2$, with energy levels of about 0.5 to about 2.5 W/cm$^2$ being preferred. Energy levels for therapeutic ultrasound involving hyperthermia are generally from about 5 W/cm$^2$ to about 50 W/cm$^2$. For very small vesicles, for example, vesicles having a diameter of less than about 0.5 micron, higher frequencies of sound are generally preferred. This is because smaller vesicles are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, for deep structures it is generally necessary to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosures of which are hereby incorporated herein by reference in their entirety.

The useful dosage to be administered and the particular mode of administration will vary depending upon such factors as the age, weight and the particular animal and region thereof to be treated, the particular amphiphilic compound or compounds used, the presence or absence of a bioactive agent, the diagnostic or therapeutic use contemplated, and the form of the involved compositions, for example, micelle or liposome, as will be readily apparent to those skilled in the art. Typically, dosage is administered at lower levels and increased until the desirable therapeutic effect is achieved. The amount of amphiphilic compound that is administered can vary and generally depends upon the amount of particular fluorinated amphiphilic compound and additional amphiphilic material, as desired, administered.

The present invention is further described in the following examples. Examples 1, 2 and 4 to 7 describe the preparation of vesicular compositions within the scope of the present invention. Example 1 also describes an evaluation of the pressure stability of a vesicular composition within the scope of the present invention and a composition prepared from a nonfluorinated amphiphilic compound. Example 3 describes the freeze-fracture analysis of vesicular compositions within the scope of the present invention. All of the examples are prophetic examples. These examples are for illustrative purposes only, and are not to be construed as limiting the appended claims.

EXAMPLES

In the following examples, reference to the compounds of formulas (V)(A), (V)(E) and (V)(F) are to the corresponding compounds set forth in Table III above. In addition, "DPPC" in Example 1 refers to dipalmitoylphosphatidylcholine.

Example 1

The compound of formula (V)(A) will be prepared using the procedures described hereinbefore. The compound will be suspended, at a concentration of 1 mg/mL, in a solution of saline: glycerol: propylene glycol (8:1:1 w/w/w). The resulting mixture (1.5 mL) will be placed into a sterile 3 mL glass vial. The head space in the vial will be replaced with perfluoropropane gas and the vial will be sealed. The vial will be shaken for 5 minutes at 4,200 r.p.m. on a Wig-L-Bug™ (Crescent Dental, Lyons, Ill.) shaking apparatus to provide perfluoropropane gas-filled vesicles (liposomes) having a mean diameter of about 3 μm. The gas-filled vesicles will be stable for several weeks at room temperature. This will be repeated except that the compound of formula (V)(A) is replaced with DPPC. The pressure stability of the vesicular composition comprising the fluorinated amphiphile of formula (V)(A) and the composition containing DPPC will be compared in an acoustic laboratory. The compositions will be exposed to elevated pressure (300 mm Hg), and the loss in attenuation and backscatter between the compositions will be compared. The vesicular composition comprising the fluorinated amphiphilic compound of formula (V)(A) will exhibit improved pressure stability.

Example 2

The compound of formula (V)(F) will be prepared as described above. A vesicular composition comprising this compound will then be prepared using the procedure described in Example 1 except that the concentration of the saline:glycerol:propylene glycol suspension will be 1.25 mg/mL and the head space of the vial will be replaced with perfluorobutane gas. The resulting perfluorobutane gas-filled vesicular composition will exhibit improved properties, including pressure stability.

Example 3

Freeze-fracture electron microscopy (FFEM), using standard techniques, will be performed on the vesicular compositions within the scope of the present invention and which were prepared in Examples 1 and 2. FFEM will show that the gas-filled vesicles of the present invention possess smooth walls having a thickness of about a single bilayer.

Example 4

The compound of formula (V)(E) will be prepared using the procedures described above. A mixture of the compound of formula (V)(E) (10 mg/mL) in normal saline with trehalose (20 mg/mL) and poloxamer F68 (polyoxyethylenepolyoxypropylene glycol block copolymer) (25 mg/mL) will be heated to 60° C. and passed through a Microfluidizer (Mircofluidics Corp., Newton, Mass.) 20 times at 16,000 psi. The resulting vesicular composition will be lyophilized and the head space of the container in which the composition is stored will be instilled gradually with nitrogen gas and reequilibrated to ambient pressure over a period of 48 hours. The resulting vesicular composition will comprise gas (nitrogen) filled vesicles (liposomes) having a mean diameter of 200 nm. The vesicles can be stored dry until use, as desired, and can be rehydrated with sterile water and shaken prior to injection.

Example 5

The compound of formula (V)(E) will be prepared as described above and suspended, at a concentration of 1 mg/mL, in a solution of saline:glycerol:propylene glycol (8:1:1 w/w/w). The resulting mixture (1.5 mL) will be placed into a sterile 3 mL glass vial at 350C. The head space in the vial will be replaced with perfluoropentane gas and the vial will be sealed. The vial will be shaken for 5 minutes at 4,200 r.p.m. on a Wig-L-Bug™ (Crescent Dental, Lyons, Ill.) shaking apparatus while the temperature of the vial is maintained at 35° C. Perfluoropentane gas-filled vesicles (liposomes) will be obtained.

Example 6

Example 5 will be repeated except that the perfluoropentane gas is replaced with a mixture of perfluoropentane gas and nitrogen gas (1:1 v/v). Cooling the resulting liposomes to below 30° C. may result in the condensation of the perfluoropentane gas. However, the condensed perfluoropentane will exist as a nanodroplet within the vesicles and can be volatilized by warming to provide the gas-filled vesicles. This warming can be caused by artificial means ex vivo or by the body temperature of a patient after administration of the vesicular composition.

Example 7

The compound of formula (V)(F) will be prepared as described above and suspended, at a concentration of 1 mg/mL, in a solution of saline:glycerol:propylene glycol (7:1.5:1.5 w/w/w). The resulting mixture (1.5 mL) will be placed into a sterile 3 mL glass vial at 60° C. The head space in the vial will be replaced with perfluorohexane gas at 60° C. The vial will be sealed and shaken for 5 minutes at 4,400 r.p.m. on a Wig-L-Bug™ (Crescent Dental, Lyons, Ill.) shaking apparatus while the temperature of the vial is maintained at 60° C. Perfluorohexane gas-filled vesicles (liposomes) will be obtained.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

What is claimed is:

1. A method for the therapeutic delivery in vivo of a bioactive agent comprising administering to a patient a therapeutically effective amount of a formulation which comprises, in combination with a bioactive agent, a stabilized vesicular composition of a fluorinated amphiphilic compound and a gas, wherein said gas is sulfur hexafluoride and is encapsulated in said vesicles which are selected from the group consisting of liposomes, micelles and microspheres, and wherein said fluorinated amphiphilic compound is of formula (II):

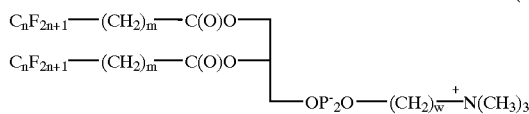

wherein:

m is 0 to about 18;
n is 1 to about 12; and
w is 1 to about 8.

2. A method according to claim 1 wherein m is about 2 to about 14;
n is about 2 to about 10; and
w is 1 to about 4.

3. A method according to claim 2 wherein m is about 4 to about 10;
n is about 4 to about 8; and
w is about 2.

4. A method according to claim 1 wherein said vesicles are selected from the group consisting of micelles and liposomes.

5. A method according to claim 1 wherein said vesicles comprise unilamellar vesicles.

6. A method according to claim 5 wherein said vesicles comprise a monolayer.

7. A method according to claim 6 wherein said lipid comprises a phospholipid.

8. A method according to claim 5 wherein said vesicles comprise a bilayer.

9. A method according to claim 8 wherein said lipid comprises a phospholipid.

10. A method according to claim 1 wherein said vesicles are selected from the group consisting of oligolamellar and multilamellar vesicles.

11. A method according to claim 1 wherein said bioactive agent is substantially entrapped within said vesicles.

12. A method according to claim 1 wherein said bioactive agent comprises genetic material.

13. A method according to claim 1 wherein said composition further comprises a gas selected from the group consisting of air, nitrogen, carbon dioxide, oxygen, fluorine, helium, argon, xenon and neon.

14. A method according to claim 1 wherein said formulation further comprises a material for targeting in vivo.

15. A method according to claim 14 wherein said targeting material is selected from the group consisting of proteins, carbohydrates, peptides, glycopeptides, glycolipids, lectins and nucleosides.

16. A method according to claim 14 which comprises intravascular targeting.

17. A method according to claim 6 wherein said lipid is a phospholipid and said gas is sulfur hexafluoride.

18. A method according to claim 6 wherein said formulation further comprises polyethylene glycol.

19. A method according to claim 8 wherein said lipid is a phospholipid and said gas is sulfur hexafluoride.

20. A method according to claim 8 wherein said formulation further comprises polyethylene glycol.

21. A method according to claim 1 wherein said composition has been reconstituted from a lyophilized composition.

22. A method according to claim 1 wherein said formulation comprises a protein.

23. A method according to claim 22 wherein said protein is crosslinked.

24. A method according to claim 1 wherein said bioactive agent is incorporated in a membrane wall of said vesicle composition.

* * * * *

UNITED STATES PATENT AND TRADEMARK OFFICE
CERTIFICATE OF CORRECTION

PATENT NO. : 5,997,898
DATED : December 7, 1999
INVENTOR(S) : Evan C. Unger

It is certified that error appears in the above-identified patent and that said Letters Patent is hereby corrected as shown below:

<u>Title page,</u>
Item [56], OTHER PUBLICATIONS, "Yeung et al.," please delete "Microencapulated" and insert -- Microencapsulated -- therefor.
"Mattrey et al.," please delete "Prelimiary" and insert -- Preliminary -- therefor.
"Mattrey et al., please delete "*Investigatvie*" and insert -- *Investigative* -- therefor.
"Keller et al.," please delete "Microcirulation" and insert -- Microcirculation -- therefor.
"Stelmashok et al.," please delete "*Koordinatsionnay*" and insert
-- *Koordinatsionnaya* -- therefor.
"Hop et al.," please delete "Hop" and insert -- Hope -- therefor.
"M.R. Zalutsky," please delete "et all." and insert -- et al. -- therefor.
"Poznansky et al.," please delete "Biologica" and insert -- Biological -- therefor.
"Villanueva et al.," please delete "Patters" and insert -- Patterns -- therefor.
"Maxweel," please delete "Maxweel" and insert -- Maxwell -- therefor.
Please add the following reference:
-- Desir et al., "Assessment of regional myocardial perfusion with myocardial contrast echocardiography in a canine model of varying degrees of coronary stenosis," *Am. Heart J.*, 1994, 127(1), 56-63 --

<u>Column 4,</u>
Line 20, please delete "reparation" and insert -- preparation -- therefor.

<u>Column 8,</u>
Line 66, please delete "$CH_2CH_2SCH_2CH_2N^+(CH_3)_3{}^{-OSO}{}_2OCH_3$" and insert
-- $CH_2CH_2SCH_2CH_2N^+(CH_3)_3\text{-}OSO_2OCH_3$ -- therefor.

Signed and Sealed this

First Day of April, 2003

JAMES E. ROGAN
*Director of the United States Patent and Trademark Office*